(12) United States Patent
Virag et al.

(10) Patent No.: US 8,580,739 B2
(45) Date of Patent: Nov. 12, 2013

(54) METHODS OF REDUCING MYOCARDIAL INJURY FOLLOWING MYOCARDIAL INFARCTION

(75) Inventors: Jitka A. I. Virag, Greenville, NC (US); Jessica L. Dries, Saint Paul, MN (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 13/299,096

(22) Filed: Nov. 17, 2011

(65) Prior Publication Data

US 2012/0122789 A1 May 17, 2012

Related U.S. Application Data

(60) Provisional application No. 61/414,741, filed on Nov. 17, 2010.

(51) Int. Cl.
*A61P 9/10* (2006.01)

(52) U.S. Cl.
USPC ........................................ 514/16.4; 514/13.3

(58) Field of Classification Search
None
See application file for complete search history.

(56) References Cited

PUBLICATIONS

Modulation of ephrinB2 leads to increased angiogenesis in ischemic myocardium and endothelial cell proliferation. Månsson-Broberg A, Biochem Biophys Res Commun. Aug. 29, 2008;373(3):355-9. Epub Jun. 20, 2008.*
Eph-ephrin bidirectional signaling in physiology and disease. Pasquale EB. Cell. Apr. 4, 2008;133(1):38-52.*
Improving regenerating potential of the heart after myocardial infarction: factor-based approach. Hwang H, Kloner RA. Life Sci. Mar. 27, 2010;86(13-14):461-72. Epub Jan. 20, 2010.*
Reperfusion injury revisited: is there a role for growth factor signaling in limiting lethal reperfusion injury? Yellon DM, Baxter GF. Trends Cardiovasc Med. Nov. 1999;9(8):245-9.*
Therapeutic angiogenesis in the heart: protect and serve. Molin D, Post MJ. Curr Opin Pharmacol. Apr. 2007;7(2):158-63. Epub Feb. 5, 2007.*
Role of B61, the ligand for the Eck receptor tyrosine kinase, in TNF-alpha-induced angiogenesis. Pandey A, Shao H, Marks RM, Polverini PJ, Dixit VM. Science. Apr. 28, 1995;268(5210):567-9.*
Eph/ephrin signaling: networks. Arvanitis D, Davy A. Genes Dev. Feb. 15, 2008;22(4):416-29.*
Concepts and consequences of Eph receptor clustering. Janes PW, Nievergall E, Lackmann M. Semin Cell Dev Biol. Feb. 2012;23(1):43-50. Epub Jan. 12, 2012.*
Neurosci Lett. Jun. 19, 2012;518(2):92-5. Epub May 3, 2012. Inhibition of EphA4 signaling after ischemia-reperfusion reduces apoptosis of CA1 pyramidal neurons. Li J, Liu N, Wang Y, Wang R, Guo D, Zhang C.*
NCBI Gene Database entry for ephrin A1.*

Arvanitis et al. "Eph/ephrin signaling: networks", *Genes Dev.* 22:416-429 (2008).
Bodor et al. "Cardiac troponin-I is not expressed in fetal and healthy or diseased adult human skeletal muscle tissue.", *Clin. Chem.* (1995) Abstract Only.
Brantley-Sieders et al. "Eph receptor tyrosine kinases in tumor and tumor microenvironment", *Curr. Pharm. Des.* (2004) Abstract Only.
Brantley-Sieders et al. "Ephrin-A1 Facilitates Mammary Tumor Metastasis through an Angiogenesis-Dependent Mechanism Mediated by EphA Receptor and Vascular Endothelial Growth Factor in Mice", *Cancer Res.* 66:10315-10324 (2006).
Braunwald et al. "ACC/AHA Guideline update for the management of patients with unstable angina and non-Ste-segment elevation myocardial infarction—2002: summary article: a report of the American College of Cardiology/American Heart Association Task Force on Practice Guidelines", *Circulation* 106:1893-1900 (2002).
Braunwald et al. "Ventricular Enlargement and Remodeling Following Acute Myocardial Infarction: Mechanisms and Management", *Am. J. Cardiol.* 68:1D-6D (1991).
Bruckner et al. "Tyrosine Phosphorylation of Transmembrane Ligands for Eph Receptors", *Science* 275:1640-1643 (1997).
Chapelle et al. "Cardiac troponin I and troponin T: recent players in the field of myocardial markers", *Clin. Chem. Lab. Med.* 37:11-20 (1999).
N. Cheng et al. "The ephrins and Eph receptors in angiogenesis", *Cytokine & Growth Factor Reviews* 13:75-85 (2002).
N. Cheng et al. "Blockade of EphA Receptor Tyrosine Kinase Activation Inhibits Vascular Endothelial Cell Growth Factor-Induced Angiogenesis", *Mol. Cancer Res.* 1:2-11 (2002).
W. Cheng et al. "Programmed Myocyte Cell Death Affects the Viable Myocardium after Infarction in Rats", *Exp. Cell Res.* 226:316-327 (1996).
Dorn et al, "Novel pharmacotherapies to abrogate postinfarction ventricular remodeling", *Nature Reviews Cardiol.* 6:283-291 (2009).
Dorn et al. "The rationale for cariomyocyte resuscitation in myocardial salvage", *J. Mol. Med.* 86:1085-1095 (2008).
Easty et al. "Up-Regulation of Ephrin-A1 During Melanoma Progression", *Int. J. Cancer. (Pred. Oncol.)* 84:494-501, (1999).
Fishbein et al. "Experimental Myocardial Infarction in the Rat", *Am. J. Pathol.* 90:57-70 (1978).
Frangogiannis "The immune system and cardiac repair", *Pharmacological Res.* 58:88-111 (2008).
Frangogiannis et al. "The inflammatory response in myocardial infarction", *Cardiovascular. Res.* 53:31-47 (2002).
Frieden et al. "Regulation of Heart Valve Morphogenesis by Eph Receptor Ligand, Ephrin-A1", *Developmental Dynamics* 239:3226-3234 (2010).
Freude et al. "Cardiomyocyte apoptosis in acute and chronic conditions", *Basic Res. Cardiol.* 93:85-89 (1998).
Gaudron et al. "Adaptation to Cardiac Dysfunction After Myocardial Infarction", *Circulation* 87(55) (1993) Abstract Only.
Goichberg et al. "The Ephrin A1-EphA2 System Promotes Cardiac Stem Cell Migration After Infarction", *Circ. Res.* 108:1-13 (2011).

(Continued)

*Primary Examiner* — Brian J Gangle
*Assistant Examiner* — Andrea McCollum
(74) *Attorney, Agent, or Firm* — Myers Bigel Sibley & Sajovec, P.A.

(57) ABSTRACT

The present invention discloses methods of reducing injury resulting from cardiovascular disease, such as myocardial infarction, and/or promoting myocardial repair. The methods include administering an ephrin and pharmaceutical compositions including ephrins to a subject. Kits useful for accomplishing the same are also provided.

12 Claims, 8 Drawing Sheets

(56) References Cited

PUBLICATIONS

Goldstein et al. "Ventricular Remodeling: Mechanisms and Prevention", *Cardiology Clinics* 16:623-632 (1998).
Hirai et al. "A Novel Putative Tyrosine Kinase Receptor Encoded by the *eph* Gene", *Science* 238:1717-1720 (1987).
Holmes et al. "Structure and Mechanics of Healing Myocardial Infarcts", *Annu. Rev. Biomed. Eng.* 7:223-253 (2005)
Iida et al. "Ephrin-A1 expression contributes to the malignant characteristics of α-fetoprotein producing hepatocellular carcinoma", *Gut* 54:843-851 (2005).
Ivanov et al. "Putative Dual Role of Ephrin-Eph Receptor Interactions in Inflammation", *IUBMB Life* 58(7):389-394 (2006).
Jaffe "Use of Biomarkers in the Emergency Department and Chest Pain Unit", *Cardiol. Clin.* 23:453-465 (2005).
Klein "Excitatory Eph receptors and adhesive ephrin ligands", *Curr. Opin. Cell Biol.* 13:196-203 (2001).
Kullander et al. "Mechanisms and Functions of EPH and Ephrin Signalling", *Nat. Rev. Mol. Cell Biol.* 3:475-486 (2002).
Lambert et al. "Macrophage roles following myocardial infarction", *Int. J. Cardiol.* 130:147-158 (2008).
Lefer et al. "Oxidative Stress and Cardiac Disease", *Am. J. Med.* 109:315-323 (2000).
MacLellan et al. "Death by Design: Programmed Cell Death in Cardiovascular Biology and Disease", *Circulation Research* 81:137-144 (1997).
Mellitzer et al. "Eph receptors and ephrins restrict cell intermingling and communication", *Nature* 400:77-81 (1999).
Moon et al. "Synthetic Biomimetic Hydrogels Incorporated with Ephrin-A1 for Therapeutic Angiogenesis", *Biomacromolecules* 8:42-49 (2007).
Munoz et al. "Thymic Alterations in EphA4-Deficient Mice", *J. Immunol.* 177:804-813 (2006).
Nageh et al. "Cardiac troponin T and I and creatine kinase-MB as markers of myocardial injury and predictors of outcome following percutaneous coronary intervention", *Int. J. Cardiol.* 92:285-293 (2003).
Nah et al. "The Inflammatory Response and Cardiac Repair After Myocardial Infarction", *Korean Circ. J.* 39:393-398 (2009).
Nakai et al. "The role of autophagy in cardiomyocytes in the basal state and in response to hemodynamic stress", *Nature Medicine* 13(5):619-624 (2007).
Ogawa et al. "The ephrin-A1 ligand and its receptor, EphA2, are expressed during tumor neovascularization", *Oncogene* 19:6043-6052, (2000).
Oyama et al. "Cardiac Troponin-I Concentration in Dogs with Cardiac Disease", *J. Vet. Intern. Med.* 18:831-839 (2004).
Pandey et al. "Role of B61, the Ligand for the Eck Receptor Tyrosine Kinase, in TNF-α-Induced Angiogenesis", *Science* 268:567-569 (1995).
Pasquale "Eph-Ephrin Bidirectional Signaling in Physiology and Disease", *Cell* 133:38-52 (2008).
Pasquale "Eph receptors and ephrins in cancer: bidirectional signalling and beyond", *Nature Reviews Cancer* 10:165-180 (2010).
Porrello et al. "Cardiomyocyte autophagy is regulated by angiotensin II type 1 and type 2 receptors", *Autophagy* 5:1515-1216 (2009).
Virag et al. "Myofibroblast and Endothelial Cell Proliferation during Murine Myocardial Infarct Repair", *Am. J. Pathol.* 163(6):2433-2440 (2003).
Wykosky et al. "Soluble monomeric EphrinA1 is released from tumor cells and is a functional ligand for the EphA2 receptor", *Oncogene* 27:7260-7273 (2008).
Zhou et al. "The Eph Family Receptors and Ligands", *Pharmacol.I Ther.* 77(3):151-181 (1998).

\* cited by examiner

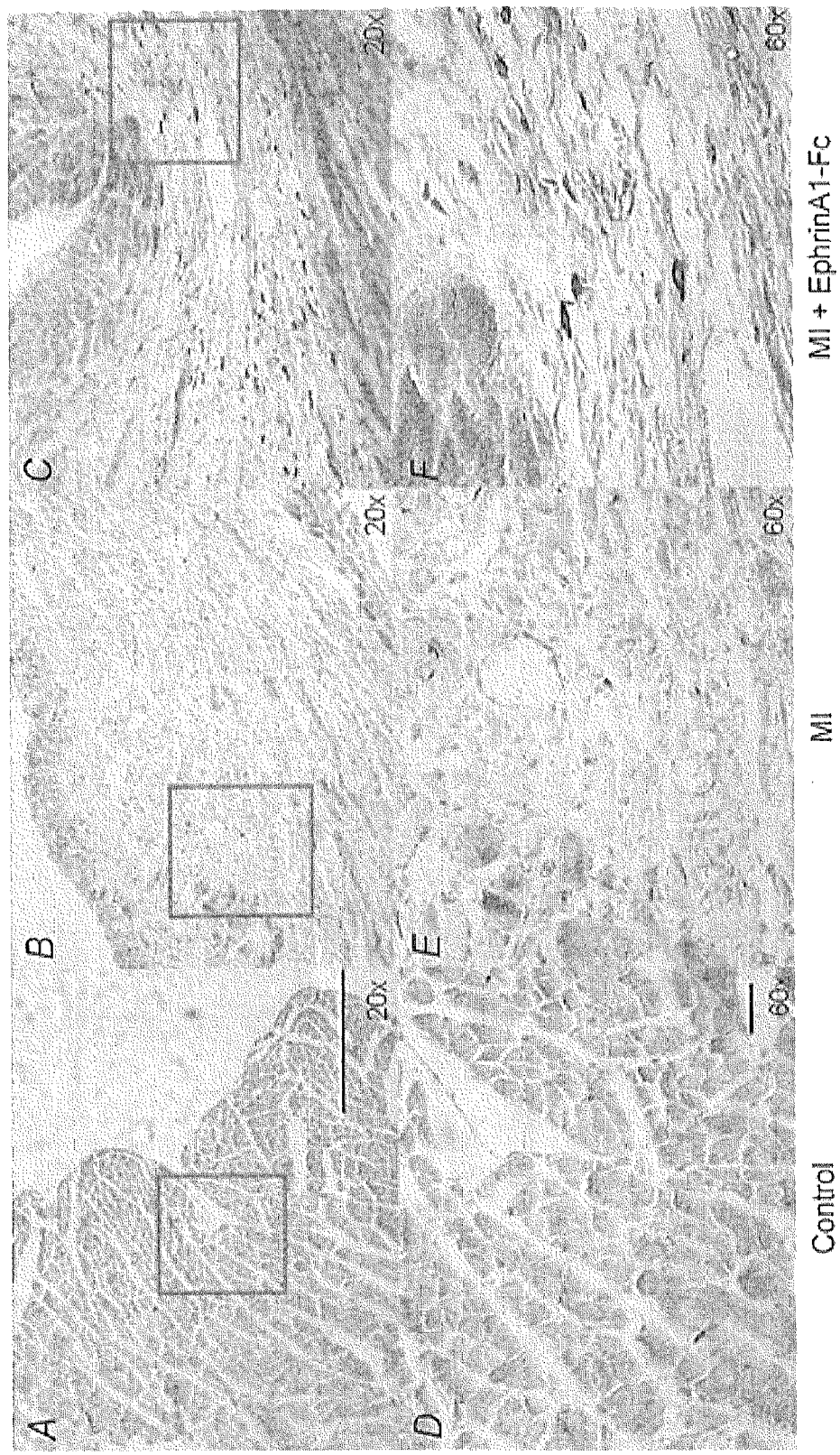
Figures 6A–F

SEQUENCE LISTING

<160> NUMBER OF SEQ ID NOS: 4

<210> SEQ ID NO 1
<211> LENGTH: 205
<212> TYPE: PRT
<213> ORGANISM: Mus musculus

<400> SEQUENCE: 1

```
Met Glu Phe Leu Trp Ala Pro Leu Leu Gly Leu Cys Cys Ser Leu Ala
1               5                   10                  15

Ala Ala Asp Arg His Ile Val Phe Trp Asn Ser Ser Asn Pro Lys Phe
            20                  25                  30

Arg Glu Glu Asp Tyr Thr Val His Val Gln Leu Asn Asp Tyr Leu Asp
        35                  40                  45

Ile Ile Cys Pro His Tyr Glu Asp Asp Ser Val Ala Asp Ala Ala Met
    50                  55                  60

Glu Arg Tyr Thr Leu Tyr Met Val Glu His Gln Glu Tyr Val Ala Cys
65                  70                  75                  80

Gln Pro Gln Ser Lys Asp Gln Val Arg Trp Asn Cys Asn Arg Pro Ser
                85                  90                  95

Ala Lys His Gly Pro Glu Lys Leu Ser Glu Lys Phe Gln Arg Phe Thr
            100                 105                 110

Pro Phe Ile Leu Gly Lys Glu Phe Lys Glu Gly His Ser Tyr Tyr Tyr
        115                 120                 125

Ile Ser Lys Pro Ile Tyr His Gln Glu Ser Gln Cys Leu Lys Leu Lys
    130                 135                 140

Val Thr Val Asn Gly Lys Ile Thr His Asn Pro Gln Ala His Val Asn
145                 150                 155                 160

Pro Gln Glu Lys Arg Leu Gln Ala Asp Asp Pro Glu Val Gln Val Leu
                165                 170                 175

His Ser Ile Gly Tyr Ser Ala Ala Pro Arg Leu Phe Pro Leu Val Trp
```

```
                        180                 185                 190
Ala Val Leu Leu Leu Pro Leu Leu Leu Leu Gln Ser Gln
            195                 200                 205

<210> SEQ ID NO 2
<211> LENGTH: 142
<212> TYPE: PRT
<213> ORGANISM: Mus musculus

<400> SEQUENCE: 2

Met Glu Arg Tyr Thr Leu Tyr Met Val Glu His Gln Glu Tyr Val Ala
1               5                   10                  15

Cys Gln Pro Gln Ser Lys Asp Gln Val Arg Trp Asn Cys Asn Arg Pro
            20                  25                  30

Ser Ala Lys His Gly Pro Glu Lys Leu Ser Glu Lys Phe Gln Arg Phe
        35                  40                  45

Thr Pro Phe Ile Leu Gly Lys Glu Phe Lys Glu Gly His Ser Tyr Tyr
    50                  55                  60

Tyr Ile Ser Lys Pro Ile Tyr His Gln Glu Ser Gln Cys Leu Lys Leu
65                  70                  75                  80

Lys Val Thr Val Asn Gly Lys Ile Thr His Asn Pro Gln Ala His Val
                85                  90                  95

Asn Pro Gln Glu Lys Arg Leu Gln Ala Asp Asp Pro Glu Val Gln Val
            100                 105                 110

Leu His Ser Ile Gly Tyr Ser Ala Ala Pro Arg Leu Phe Pro Leu Val
        115                 120                 125

Trp Ala Val Leu Leu Leu Pro Leu Leu Leu Gln Ser Gln
    130                 135                 140

<210> SEQ ID NO 3
<211> LENGTH: 205
<212> TYPE: PRT
<213> ORGANISM: Homo sapiens

<400> SEQUENCE: 3

Met Glu Phe Leu Trp Ala Pro Leu Leu Gly Leu Cys Cys Ser Leu Ala
1               5                   10                  15

Ala Ala Asp Arg His Thr Val Phe Trp Asn Ser Ser Asn Pro Lys Phe
            20                  25                  30

Arg Asn Glu Asp Tyr Thr Ile His Val Gln Leu Asn Asp Tyr Val Asp
        35                  40                  45

Ile Ile Cys Pro His Tyr Glu Asp His Ser Val Ala Asp Ala Ala Met
    50                  55                  60

Glu Gln Tyr Ile Leu Tyr Leu Val Glu His Glu Glu Tyr Gln Leu Cys
65                  70                  75                  80

Gln Pro Gln Ser Lys Asp Gln Val Arg Trp Gln Cys Asn Arg Pro Ser
                85                  90                  95

Ala Lys His Gly Pro Glu Lys Leu Ser Glu Lys Phe Gln Arg Phe Thr
            100                 105                 110

Pro Phe Thr Leu Gly Lys Glu Phe Lys Glu Gly His Ser Tyr Tyr Tyr
        115                 120                 125

Ile Ser Lys Pro Ile His Gln His Glu Asp Arg Cys Leu Arg Leu Lys
    130                 135                 140

Val Thr Val Ser Gly Lys Ile Thr His Ser Pro Gln Ala His Asp Asn
145                 150                 155                 160

Pro Gln Glu Lys Arg Leu Ala Ala Asp Asp Pro Glu Val Arg Val Leu
                165                 170                 175
```

```
His Ser Ile Gly His Ser Ala Ala Pro Arg Leu Phe Pro Leu Ala Trp
            180                 185                 190

Thr Val Leu Leu Leu Pro Leu Leu Leu Leu Gln Thr Pro
            195                 200                 205

<210> SEQ ID NO 4
<211> LENGTH: 183
<212> TYPE: PRT
<213> ORGANISM: Homo sapiens

<400> SEQUENCE: 4

Met Glu Phe Leu Trp Ala Pro Leu Leu Gly Leu Cys Cys Ser Leu Ala
1               5                   10                  15

Ala Ala Asp Arg His Thr Val Phe Trp Asn Ser Ser Asn Pro Lys Phe
            20                  25                  30

Arg Asn Glu Asp Tyr Thr Ile His Val Gln Leu Asn Asp Tyr Val Asp
        35                  40                  45

Ile Ile Cys Pro His Tyr Glu Asp His Ser Val Ala Asp Ala Ala Met
50                  55                  60

Glu Gln Tyr Ile Leu Tyr Leu Val Glu His Glu Glu Tyr Gln Leu Cys
65                  70                  75                  80

Gln Pro Gln Ser Lys Asp Gln Val Arg Trp Gln Cys Asn Arg Pro Ser
                85                  90                  95

Ala Lys His Gly Pro Glu Lys Leu Ser Glu Lys Phe Gln Arg Phe Thr
            100                 105                 110

Pro Phe Thr Leu Gly Lys Glu Phe Lys Glu Gly His Ser Tyr Tyr Tyr
        115                 120                 125

Ile Ser His Ser Pro Gln Ala His Asp Asn Pro Gln Glu Lys Arg Leu
130                 135                 140

Ala Ala Asp Asp Pro Glu Val Arg Val Leu His Ser Ile Gly His Ser
145                 150                 155                 160

Ala Ala Pro Arg Leu Phe Pro Leu Ala Trp Thr Val Leu Leu Leu Pro
                165                 170                 175

Leu Leu Leu Leu Gln Thr Pro
            180
```

METHODS OF REDUCING MYOCARDIAL INJURY FOLLOWING MYOCARDIAL INFARCTION

CROSS-REFERENCE TO RELATED APPLICATION

This application claims the benefit of, and incorporates herein by reference in its entirety, U.S. Provisional Application No. 61/414,741, filed Nov. 17, 2010.

FIELD OF THE INVENTION

The present invention concerns methods of reducing injury resulting from cardiovascular disease or events, such as myocardial infarction, and/or promoting myocardial repair. The present invention further concerns pharmaceutical compositions and kits useful for accomplishing the same.

BACKGROUND OF THE INVENTION

The heart generally lacks an endogenous regenerative capacity sufficient for repair after injury. Consequential left ventricular (LV) remodeling after myocardial infarction (MI) leads to LV dilatation, ultimately leading to heart failure (Pfeffer & Braunwald, 1991; Gaudron et al., 1993; Goldstein et al., 1998; Holmes et al., 2005). To reduce this epidemiologic and fiscal burden, it is imperative that strategies be developed to preserve cardiomyocyte survival, subsequently reducing myocardial infarct size, and reducing overall LV remodeling.

Immediately after coronary occlusion, ischemic myocytes downstream from the occlusion become necrotic and/or undergo apoptosis (Cheng et al., 1996; MacLellan & Schneider, 1997; Freude et al., 1998) or autophagy (Nakai et al., 2007; Dorn & Diwan, 2008; Porrello & Delbridge, 2009). Cardiac troponin I is released, which can be measured in plasma and correlates to the size of injury (Bodor et al., 1995; Chapelle, 1999; Braunwald et al., 2002; Nageh et al., 2003; Oyama & Sisson, 2004; Jaffe, 2005). Neutrophils infiltrate the tissue immediately, while leukocytes, predominantly macrophages, arrive shortly thereafter and participate in digestion of necrotic cellular debris. Neutrophils in the ischemic tissue can be toxic to the surrounding myocytes, because they release reactive oxygen species and proteolytic enzymes which further injure the surrounding myocytes (Lefer & Granger, 2000; Frangogiannis et al., 2002; Frangogiannis, 2008; Lambert et al., 2008; Nah & Rhee, 2009). Once damage occurs, a hypocellular scar forms that leads to contractile dysfunction and heart failure (Fishbein et al., 1978; Frangogiannis et al., 2002; Virag & Murry, 2003; Dorn, 2009).

Since the discovery of the Eph (erythropoietin-producing hepatocellular carcinoma) receptor tyrosine kinase (RTKs) in 1987 (Hirai et al., 1987), a great deal of effort has been focused on elucidating Eph receptor tyrosine kinase (RTK) and ephrin ligand signaling in the context of numerous pathologies. A distinguishing characteristic of Eph-ephrin interactions is the ability to generate bidirectional signaling. "Forward" signaling occurs in the direction of the receptor-expressing cell, while "reverse" signaling occurs in the direction of the ligand expressing cell (Bruckner et al., 1997; Mellitzer et al., 1999; Klein, 2001; Kullander & Klein, 2002). Upon ligand binding and receptor activation, endocytic internalization of the complex occurs (Pasquale, 2010), leading to downregulation of the protein. Intracellular cascades downstream of Eph/ephrin signaling are involved in cellular survival, growth, differentiation, and motility (Zhou, 1998; Kullander & Klein, 2002; Arvanitis & Davy, 2008; Pasquale, 2008, 2010). The EphA1 receptor has been linked to angiogenesis through endothelial cell migration. Like the ephrinA1 ligand, EphA1 is induced by TNF-a, VEGF, and leading to cellular adhesion via integrins and vessel destabilization (Pandey et al., 1995; Cheng et al., 2002a; Cheng et al., 2002b; Moon et al., 2007). Similarly, the EphA2 receptor, expressed on endothelial cells, is widely reported as a key player in angiogenesis, particularly in development and cancer (Ogawa et al., 2000; Brantley-Sieders et al., 2004; Brantley-Sieders et al., 2006; Wykosky et al., 2008).

Of the at least five ephrinA ligands, ephrinA1 is unique in that it is currently the only ligand that binds all eight EphA receptors known to be expressed in mice. Aside from its predominant characterization as a pro-angiogenic factor in adult mouse tumors, (Easty et al., 1999; Ogawa et al., 2000; Iida et al., 2005), ephrinA1 appears to be involved in inflammation and apoptosis. It was reported in 2006 that Eph receptors are differentially expressed at early and late stages of inflammation (Ivanov & Romanovsky, 2006). For example, at earlier stages of inflammation, EphA2 and EphrinB2 expression is predominantly localized to epithelial and endothelial cells, promoting disruption of the endothelial/epithelial barrier. However, as the inflammatory process progresses, expression of EphA1, EphA3, EphB3, and EphB4 on these cells decreases, allowing infiltrating leukocytes to adhere to endothelial cells by disrupting endothelial/epithelial barriers (Ivanov & Romanovsky, 2006). EphrinA1/EphA receptor expression changes also appear to be involved in regulating pathways involved with apoptosis. In 2006, Munoz and colleagues reported that EphA4 deficient mice exhibited both defective T cell development and increased numbers of apoptotic cells (Munoz et al., 2006).

SUMMARY OF THE INVENTION

Embodiments of the present invention provide methods of reducing injury following cardiovascular events or disease in a subject in need thereof, comprising administering to the subject a therapeutically effective amount of an ephrin. Further embodiments of the present invention provide administering the ephrin at the time of onset of the cardiovascular event or disease, after awareness of the cardiovascular event or disease and/or before the onset of the cardiovascular event or disease.

Embodiments of the present invention provide methods of reducing injury following myocardial infarction in a subject in need thereof, comprising administering to the subject a therapeutically effective amount of an ephrin. Further embodiments of the present invention provide administering the ephrin at the time of myocardial infarction, after myocardial infarction and/or before myocardial infarction.

Embodiments of the present invention also provide methods of promoting myocardial repair following myocardial injury in a subject in need thereof, comprising administering to the subject a therapeutically effective amount of an ephrin. According to particular embodiments, the ephrin can be administered at the time of myocardial infarction, after myocardial infarction and/or before myocardial infarction.

Embodiments of the present invention further provide methods of reducing myocardial injury and/or promoting mycocardial repair in reperfused or nonreperfused myocardial tissue.

Further embodiments of the present invention provide a pharmaceutical composition comprising an ephrin and a pharmaceutically acceptable carrier. In some embodiments, the pharmaceutical composition further comprises an agent useful for treating cardiovascular events or disease. In some embodiments, the agent is useful for treating myocardial infarction.

A still further embodiment of the present invention provides a kit comprising a composition comprising an ephrin in a pharmaceutically acceptable carrier and a container suitable for delivery of the composition into a parental delivery system. In some embodiments, the parenteral delivery system is an intramyocardial administration device.

The foregoing and other embodiments of the present invention are explained in greater detail throughout.

DETAILED DESCRIPTION

Figure 1:
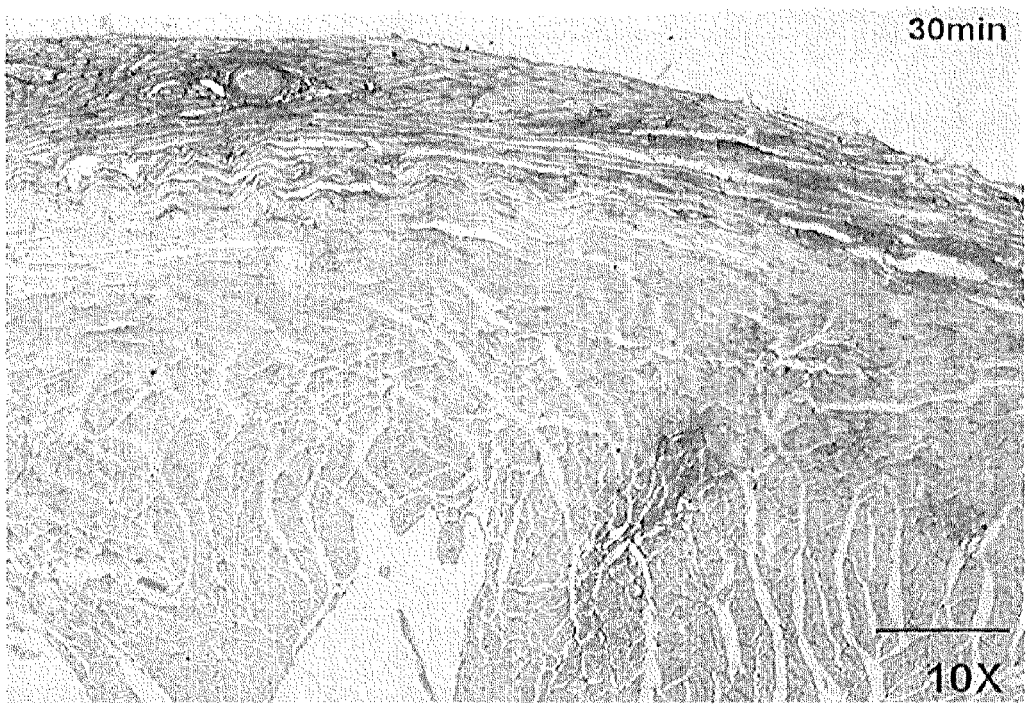
FIG. 1. EphrinA1-Fc distribution in the infarcted myocardium. Anti-human IgG-Fc staining to detect exogenous ephrinA1-Fc in the myocardium 30 min after injection. This representative image shows an abundant concentration of ephrinA1-Fc on the epicardial surface, as well as transmural expression of the protein. To a lesser extent, ephrinA1-Fc was also detected 4 hours post-injection, but could not be detected 24 hours or 4 days post-injection. Scale bar, 200 µm.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention pertains. The terminology used in the description of the invention herein is for the purpose of describing particular embodiments only and is not intended to be limiting of the invention. As used in the description of the invention and the claims set forth herein, the singular forms "a," "an," and "the" are intended to include the plural forms as well, unless the context clearly indicates otherwise.

All publications, patent applications, patents and other references cited herein are incorporated by reference in their entireties for the teachings relevant to the sentence and/or paragraph in which the reference is presented.

As used herein, the phrase "reducing injury" refers to any type of action or treatment that imparts an effect to decrease, minimize or even maintain the level of injury. Accordingly, reducing injury indicates that the subject's condition is not worsened and may be improved with respect to the injury of concern as compared with the level of injury in the absence of treatment or action described herein to reduce injury.

As used herein, "cardiovascular disease" or "heart disease" is a term used to describe a range of diseases or events that affect the heart and/or vasculature. Types of heart disease include, but are not limited to, coronary heart disease, cardiomyopathy, ischemic heart disease, heart failure, inflammatory heart disease, valvular heart disease and aneurysm. Heart disease can be assessed using clinical parameters and/or assessments known to those skilled in the art of diagnosing and/or treating the same, for example, physical examinations, detection of signs and symptoms of cardiovascular disease, electrocardiogram, echocardiogram, chest X-ray, blood tests to detect cardiac biomarkers, etc. Biomarkers typically used in the clinical setting include, but are not limited to, cardiac troponins (C, T, and I), CK and CK-MB, and myoglobin.

As used herein, "myocardial infarction" or "MI" refers to a rapid development of myocardial necrosis, which may be caused by the interruption of blood supply to the heart resulting in a critical imbalance between oxygen supply and demand of the myocardium This may result from plaque rupture with thrombus formation in a coronary vessel leading to an acute reduction of blood supply to a portion of the myocardium; that is, an occlusion or blockage of a coronary artery following the rupture of a susceptible atherosclerotic plaque. If untreated for a sufficient period of time, the resulting ischemia or restriction in blood supply and oxygen shortage can cause damage or death, i.e., infarction of the heart. In general, this damage is largely irreversible, and clinical therapies thus far mainly aim at delaying the progression of heart failure to prolong survival. Myocardial infarction can be assessed using clinical parameters and/or assessments known to those skilled in the art of diagnosing and/or treating the same, for example, physical examinations, detection of signs and symptoms of myocardial infarction, electrocardiogram, echocardiogram, chest X-ray, blood tests to detect cardiac biomarkers including troponins, CK, and CK-MB, etc.

As used herein, "reperfusion" refers to the restoration of blood flow or supply to the myocardium or myocardial tissue that has become ischemic or hypoxic. Modalities for reperfusion include, but are not limited to, chemical dissolution of the occluding thrombus, i.e., thrombolysis, administration of vasodilators, angioplasty, percutaneous coronary intervention (PCI), catheterization and coronary artery bypass graft (CABG) surgery.

As used herein, "ephrin" or "ephrins" (erythropoietin-producing hepatocellular (Eph)/Eph receptor interacting proteins refers to a family of membrane-attached proteins that are ligands of class V (EPH-related) receptor protein-tyrosine kinases. Ephrins are divided into the ephrin-A (EFNA) class, which are anchored to the membrane by a glycosylphosphatidylinositol linkage, and the ephrin-B (EFNB) class, which are transmembrane proteins. Ephrin-A (EFNA) class includes ephrin A1, ephrin A2, ephrin A3, ephrin A4 and ephrin A5, as well as variants and isoforms thereof. Ephrin-B (EFNB) class includes ephrin B 1, ephrin B2 and ephrin B3, as well as variants and isoforms thereof.

According to embodiments of the present invention, ephrins employed in the methods described herein include the full length polypeptide, polypeptide fragments of the full length polypeptide, variants and isoforms of the ephrin, fusion proteins and/or chimeric proteins comprising, consisting essentially of, and/or consisting of an ephrin or a polypeptide fragment of an ephrin joined to an exogenous polypeptide sequence, and immunogenic fragments of the ephrin. Non-limiting examples of polypeptide sequences of ephrin A1, and isoforms thereof, include human (Accession Nos. P20827.2, AAH32698.1, NP_004419.2 and NP_872626.1), mouse (Accession Nos. P52793.1, NP_034237.3 and NP_001155897.1), wild boar (Accession No. NP_001116582.1), cattle (Accession No. NP_001029464.1), zebrafish (Accession No. NP_95077.2), dog (XP_547553.1 and XP_852071.1), *xenopus laevis* (Accession Nos. NP_001088798.1 and NP_001081390.1), rat (Accession No. NP_446051.2), chimpanzee (Accession Nos. X_001141980.2 and XP_003308473.1) and *Xenopus tropicalis* (Accession No. NP_001011206.1) sequences, as well as sequences of synthetic constructs (Accession Nos. ABM81648.1, AAX42510.1 and AAX29949.1).

The ephrin may be mammalian, non-mammalian, recombinant, purified, non-purified or a crude extract comprising an ephrin. In some embodiments, the ephrin belongs to the ephrin-A class of ephrins. In further embodiments, the ephrin is ephrin A1, ephrin A2, ephrin A3, ephrin A4, ephrin A5, or a combination thereof. In still other embodiments, the ephrin is ephrin A1.

In some embodiments, the polypeptide sequence for isoform 1 of ephrin A1 from mouse is:

```
                                                            (SEQ ID NO: 1)
  1 meflwapllg lccslaaadr hivfwnssnp kfreedytvh vqlndyldii cphyeddsva 61 daamerytly mvehqeyvac qpqskdqvrw ncnrpsakhg peklsekfqr ftpfilgkef 121 keghsyyyis kpiyhqesqc lklkvtvngk ithnpqahvn pqekrlqadd pevqvlhsig 181 ysaaprlfpl vwavlllpll llqsq.
```

In another embodiment, the polypeptide sequence for isoform 2 of ephrin A1 from mouse is:

```
                                                            (SEQ ID NO: 2)
  1 merytlymve hqeyvacqpq skdqvrwncn rpsakhgpek lsekfqrftp filgkefkeg 61 hsyyyiskpi yhqesqclkl kvtvngkith npqahvnpqe krlqaddpev qvlhsigysa 121 aprlfplvwa vlllpllllq sq.
```

In another embodiment, the polypeptide sequence for isoform 1 of ephrin A1 from human is:

```
                                                            (SEQ ID NO: 3)
  1 meflwapllg lccslaaadr htvfwnssnp kfrnedytih vqlndyvdii cphyedhsva 61 daameqyily lveheeyqlc qpqskdqvrw qcnrpsakhg peklsekfqr ftpftlgkef 121 keghsyyyis kpihqhedrc lrlkvtvsgk ithspqandn pqekrlaadd pevrvlhsig 181 hsaaprlfpl awtvlllpll llqtp.
```

In another embodiment, the polypeptide sequence for isoform 2 of ephrin A1 from human is:

```
                                                                (SEQ ID NO: 4)
  1 meflwapllg lccslaaadr htvfwnssnp kfrnedytih vqlndyvdii cphyedhsva 61 daameqyily lveheeyqlc qpqskdqvrw qcnrpsakhg peklsekfqr ftpftlgkef 121 keghsyyyis hspqandnpq ekrlaaddpe vrvlhsighs aaprlfplaw tvlllpllll 181 qtp.
```

In further embodiments, the ephrin may comprise, consist essentially of, and/or consist a fragment of the full length polypeptide as set forth in any of SEQ ID NOS:1-4. In an embodiment, this fragment may comprise, consist essentially of, and/or consist of the extracellular domain of the ephrin. In a particular embodiment, the fragment may be amino acids 1-182 of SEQ ID NO:1. In another particular embodiment, the fragment may be amino acids 1-182 of SEQ ID NO:3. In yet another particular embodiment, the fragment may be amino acids 22-131 of SEQ ID NO:3.

In particular embodiments, the ephrin comprises, consists essentially of and/or consists of a fusion and/or chimeric protein that comprises, consists essentially of and/or consists of a polypeptide fragment of an ephrin fused to an exogenous peptide sequence. In particular embodiments, the exogenous peptide sequence of the fusion and/or chimeric protein is the Fc region of human IgG (where there are at least four IgG subtypes—$IgG_1$, $IgG_2$, $IgG_3$ and $IgG_4$), in particular $IgG_1$. In further embodiments, the ephrin is mouse ephrin A1-Fc. Mouse ephrin A1-Fc is a chimeric protein that comprises the extracellular domain of mouse ephrin-A1 fused by means of a polypeptide linker to the Fc region of human $IgG_1$. In still further embodiments, the ephrin is human ephrin A1-Fc. Human ephrinA1-Fc is a chimeric protein that comprises the extracellular domain of human ephrin A1 fused to the Fc region of human $IgG_1$. In still further embodiments, the ephrin may be a disulfide-linked homodimer.

The present invention further includes the use of homologs, as well as methods of obtaining homologs, of the polypeptides and/or fragments employed in this invention. As used herein, an amino acid sequence or protein is defined as a homolog of a polypeptide or fragment of the present invention if it shares significant homology or identity to one of the polypeptides and/or fragments of the present invention. Significant homology means at least 60%, 65%, 75%, 80%, 81%, 82%, 83%, 84%, 85%, 86%, 87%, 88%, 89%, 90%, 91%, 92%, 93%, 94%, 95%, 96%, 91%, 92%, 93%, 94%, 95%, 96%, 97%, 98%, 99% and/or 100% homology with another amino acid sequence. Significant identity means at least 60%, 65%, 75%, 80%, 81%, 82%, 83%, 84%, 85%, 86%, 87%, 88%, 89%, 90%, 91%, 92%, 93%, 94%, 95%, 96%, 97%, 98%, 99% and/or 100% identity with another amino acid sequence.

In further embodiments, the present invention may comprise, consist essentially of and/or consist of nucleic acids that encode the polypeptides and/or fragments that comprise the ephrins as set forth herein. These nucleic acids can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct that comprises a nucleic acid encoding a polypeptide and/or biologically active fragment employed in this invention.

The present invention further includes a vector comprising a nucleic acid encoding a polypeptide and/or fragment employed in this invention. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols.

As used herein, the term "protein" or "polypeptide" is used to describe a chain of amino acids that correspond to those encoded by a nucleic acid. A polypeptide or protein of this invention can be a peptide, which usually describes a chain of amino acids of from two to about 30 amino acids. The term polypeptide as used herein also describes a chain of amino acids having more than 30 amino acids and can be a fragment or domain of a protein or a full length protein. Furthermore, as used herein, the term polypeptide can refer to a linear chain of amino acids or it can refer to a chain of amino acids that has been processed and folded into a functional protein. It is understood, however, that 30 is an arbitrary number with regard to distinguishing peptides and polypeptides and the terms can be used interchangeably for a chain of amino acids. The polypeptides of the present invention can be obtained by isolation and purification of the polypeptides from cells where they are produced naturally, by enzymatic (e.g., proteolytic) cleavage, and/or recombinantly by expression of nucleic acid encoding the polypeptides or fragments of this invention. The polypeptides and/or fragments employed in this invention can also be obtained by chemical synthesis or other known protocols for producing polypeptides and fragments.

The term "fragment," as applied to a polypeptide, will be understood to mean an amino acid sequence of reduced length relative to a reference or full length polypeptide or amino acid sequence and comprising, consisting essentially of, and/or consisting of an amino acid sequence of contiguous amino acids identical or almost identical (e.g., 90%, 91%, 92%, 93%, 94%, 95%, 96%, 97%, 98%, 99% and/or 100% identical) to the reference or full length polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 55, 60, 65, 70, 75, 80, 85, 90, 95, 100, 110, 125, 150, 175, 182, 200, or more consecutive amino acids, including without limitation any lengths within these ranges not explicitly recited herein of consecutive amino acids up to the full length of a polypeptide or amino acid sequence according to the invention.

The amino acid sequences of this invention are presented in the amino to carboxy direction, from left to right. Any nucleotide sequences are presented in the 5' to 3' direction, from left to right. Nucleic acids can be either single or double stranded (i.e., including the complementary nucleic acid). A nucleic acid can be the complement (e.g., complementary to the full length or only to a portion) of a nucleic acid described.

The present invention further includes isolated polypeptides, peptides, proteins, fragments, domains and/or nucleic acid molecules that encode polypeptides and fragments thereof that are substantially equivalent to those described for the embodiments of this invention. As used herein, "isolated" polypeptide means a polypeptide that is separated or substantially free from at least some of the other components of the naturally occurring organism or virus, for example, the cell or viral structural components or other polypeptides or nucleic acids commonly found associated with the polypeptide. In particular embodiments, the "isolated" polypeptide is at least about 1%, 5%, 10%, 25%, 50%, 60%, 70%, 75%, 80%, 85%, 90%, 95%, 97%, 98%, 99% or more pure (w/w). In other embodiments, an "isolated" polypeptide indicates that at least about a 5-fold, 10-fold, 25-fold, 100-fold, 1000-fold, 10,000-fold, or more enrichment of the protein (w/w) is achieved as compared with the starting material.

As used herein, "substantially equivalent" can refer both to nucleic acid and amino acid sequences, for example a mutant sequence, that varies from a reference sequence by one or more substitutions, deletions, or additions, the net effect of which does not result in an undesirable adverse functional dissimilarity between reference and subject sequences. In some embodiments, this invention can include substantially equivalent sequences that have an adverse functional dissimilarity. For purposes of the present invention, sequences having equivalent biological activity and equivalent expression characteristics are considered substantially equivalent. Moreover, "substantially equivalent" can refer to the biological activity of polypeptide fragments, domains, portions, etc. having about 50%, 60%, 75%, 85%, 90%, 95%, 97%, 98%, 99%, or more, of the biological activity of the native polypeptide (and can even have a higher level of activity than the native polypeptide).

As used herein, "therapeutically effective amount" refers to an amount of an agent, i.e., ephrin, or composition that is sufficient to produce the desired therapeutic effect. The therapeutically effective amount will vary with the age and physical condition of the subject, the severity of the disorder, the duration of the treatment, the nature of any concurrent treatment, the pharmaceutically acceptable carrier used, and like factors within the knowledge and expertise of those skilled in the art. An appropriate "therapeutically effective amount" in any individual case can be determined by one of ordinary skill in the art by reference to the pertinent texts and literature and/or by using routine experimentation. (See, for example, Remington, *The Science and Practice of Pharmacy* 20th Edition, Lippincott Williams & White, Baltimore, Md. (2000).

The therapeutically effective amount, the use of which is in the scope of present invention, will vary somewhat from subject to subject, and will depend upon factors such as the age and condition of the subject and the route of delivery. Such dosages can be determined in accordance with routine pharmacological procedures known to those skilled in the art. For example, an ephrin of the present invention can be administered to the subject in an amount ranging from a lower limit of about 0.01, 0.02. 0.03, 0.04, 0.05, 0.06, 0.07, 0.08, 0.09, or 0.1 mg to an upper limit of about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, or 10.0 mg in a single dose; in an amount ranging from a lower limit of about 0.01, 0.02. 0.03, 0.04, 0.05, 0.06, 0.07, 0.08, 0.09, or 0.1 mg to an upper limit of about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0 or 20.0 mg in a 24 hour period; and as much as 30, 40, 50, 60, 70, 80, 90, 100, 200, 300, 400, 500 mg or more over a prolonged period of time with a medical infusion pump (external or implanted) or similar device designed for delivery of a substance over a prolonged period. The frequency of administration can be one, two, three, four, five times or more per day or as necessary to control the condition. The duration of therapy depends on the type of condition being treated and can be for as long as the life of the subject. In humans, the United States Food and Drug Administration (FDA) defines the maximum recommended therapeutic dose (MRTD) as 0.00001 to 1000 mg/kg body weight per day (Contrera 2004), and this dose would be dependent on the route of administration (i.e, systemically vs. directly into the heart).

As used herein, a "pharmaceutically acceptable carrier" according to the present invention is a component such as a carrier, diluent, or excipient of a composition that is compatible with the other ingredients of the composition in that it can be combined with the agents and/or compositions of the present invention without eliminating the biological activity of the agents or the compositions, and is suitable for use in subjects as provided herein without undue adverse side effects (such as toxicity, irritation, allergic response, and death). Side effects are "undue" when their risk outweighs the benefit provided by the pharmaceutical composition. Non-limiting examples of pharmaceutically acceptable components include, without limitation, any of the standard pharmaceutical carriers such as phosphate buffered saline solutions, water, sterile water, polyethylene glycol, polyvinyl pyrrolidone, lecithin, arachis oil, sesame oil, emulsions such as oil/water emulsions or water/oil emulsions, microemulsions, and various types of wetting agents. Additives such as water, alcohols, oils, glycols, preservatives, flavoring agents, coloring agents, suspending agents, and the like may also be included in the composition along with the carrier, diluent, or excipient.

"Kit" as used herein refers to an assembly of components. The assembly of components can be a partial or complete assembly. Instructions for use of the kit or use of various components of the kit are optionally included.

As used herein, "administered at the time of" means that the ephrin or composition including an ephrin according to embodiments of the present invention is administered at a time sufficiently close to the onset of an impetus causing injury, a time sufficiently close to the onset of the actual injury or a time sufficiently close to the manifestation of physical symptoms characteristic of the injury. If administered at the time of injury, the ephrin or composition including an ephrin according to embodiments of the present invention may reduce injury or prevent further injury. "Administered after" means that the ephrin or composition including an ephrin according to embodiments of the present invention is administered after the onset of an impetus causing injury, after the onset of the actual injury or after the manifestation of physical symptoms characteristic of the injury. If administered after injury, the ephrin or composition including an ephrin according to embodiments of the present invention may reduce injury or prevent further injury. "Administered before" means that the ephrin or composition including an ephrin according to embodiments of the present invention is administered before the onset of an impetus causing injury, before the onset of the actual injury or before the manifestation of physical symptoms characteristic of the injury. If administered before, the ephrin or composition including an ephrin according to embodiments of the present invention may be used as a preventive treatment.

In view of the foregoing, embodiments according to the present invention relate to methods of reducing injury following cardiovascular disease in a subject in need thereof, comprising administering to the subject a therapeutically effective amount of an ephrin. That is, injury in the presence of a therapeutically effective amount of ephrin is less than that in the absence of ephrin or does not worsen substantially in the presence of ephrin thereby reducing the extent of injury that may occur following cardiovascular disease. In particular embodiments, cardiovascular disease comprises myocardial infarction. In still other embodiments, the cardiovascular disease comprises heart failure, peripheral arterial disease or stroke.

Embodiments of the present invention address injury that may occur to the cardiovascular system, including the heart, arteries, veins, arterioles, venules, and capillaries. In some embodiments, the type of injury may include, but is not limited to, infarct size, necrosis, chamber dilation, wall thinning, inflammation, apoptotic cell death, autophagy, hypertrophy of remote myocardium, fibrosis, or a combination thereof.

According to embodiments of the present invention, the ephrin is administered at the time of the injury. In other embodiments, the ephrin is administered after the injury. In still other embodiments, the ephrin is administered before the injury.

In some embodiments of the present invention, the ephrin is administered to a subject believed to be at risk for injury to the cardiovascular system. In some embodiments, the subject is believed to be at risk for myocardial infarction. Subjects at risk for injury to the cardiovascular system or at risk for myocardial infarction can be determined by use of clinical parameters and/or assessments known to those skilled in the art of diagnosing and/or treating the same, for example, physical examinations, detection of signs and symptoms of heart disease, or myocardial infarction specifically, electrocardiogram, echocardiogram, chest X-ray, blood tests to detect cardiac biomarkers, etc.

Embodiments of the present invention further include methods of promoting myocardial repair following cardiovascular disease in a subject in need thereof, comprising administering to the subject a therapeutically effective amount of an ephrin. That is, injury to the myocardium may be repaired, e.g., reversed or maintained at the same or similar level in the presence of a therapeutically effective amount of ephrin compared to that observed in the absence of ephrin following cardiovascular disease. In particular embodiments, the cardiovascular disease is myocardial infarction. The ephrins suitable for use in such embodiments of the present invention have been described previously herein.

In some embodiments of the present invention, myocardial repair can be an improvement or a decrease in infarct size, necrosis, apoptosis, autophagy, angiogenesis, remodeling, chamber dilation, wall thinning, inflammation, reduction in serum cardiac troponin I and/or other markers of cardiomyocyte degradation or a combination thereof.

In further embodiments of the present invention, the ephrin is administered at the time of the onset of heart disease. In other embodiments, the ephrin is administered after the onset of heart disease. In still other embodiments, the ephrin is administered before the onset of heart disease.

According to further embodiments of the present invention, ephrins can be administered as an adjunct to (or in combination with) reperfusion therapy. In particular, ephrin therapy can be administered (a) at the time of injury, (b) at the time of reperfusion, (c) during reperfusion and/or (d) at the time of injury and during reperfusion. The ephrin may be administered from 0, 1, 2, 3, 4, 5, 6, 7, 8, 9, 10, 12, 15, 30, 60, 90, 120, 180, 240, 300 or 360 minutes before the time of reperfusion, or the ephrin may be administered at any period of time from the time of injury before and up to the time of reperfusion. The ephrin may further be administered every 1, 2, 3, 4, 5, 6, 7, 8, 9, 10, 15, 20, or 30 minutes or more during the first hour of reperfusion, or any number of times during the first hour of reperfusion. Alternatively, the ephrin may be administered via a slow release to provide a more constant dosage level of ephrin for a period of time such as days or weeks before, at the time of and during reperfusion.

Embodiments of the present invention further provide pharmaceutical compositions that comprise, consist essentially of or consist of an ephrin and a pharmaceutically acceptable carrier. The ephrin can be any ephrin as described herein.

In some embodiments, the pharmaceutical composition includes at least one agent useful for treating myocardial infarction and/or reducing myocardial injury. Agents that may be useful in a combination therapy with an ephrin, include, but are not limited to, thrombolytics, antiplatelet agents, anticoagulants, beta blockers, angiotensin-converting enzyme (ACE) inhibitors, 3-hydroxy-3-methylglutaryl (HMG)-CoA reductase inhibitors, glycosides, diuretics, aldosterone receptor modulators and further including agents such as statins, digoxin, SDF-1a, Thymosin B4, VEGF, IGF and those that promote progenitor cell homing to the site of injury, enhance revascularization, and/or cell survival. Ephrins can be administered in combination with stem cell therapy to promote survival, adhesion, retention of transplanted cells. "In combination" means that the two agents, compounds and/or therapies are administered closely enough in time that the presence of one alters the biological effects of the other. The two may be administered simultaneously (i.e., concurrently) or sequentially. Simultaneous administration may be carried out by mixing prior to administration, or by administering at the same point in time but at different anatomic sites or using different routes of administration. Further, the phrases "concurrent administration," "administration in combination," "simultaneous administration" or "administered simultaneously" can be employed interchangeably. Moreover, the pharmaceutical compositions of the present invention may be used and/or administered in the same manner as described herein for the use and administration of the ephrin.

Embodiments of the present invention also provide kits comprising a composition comprising, consisting essentially of or consisting of an ephrin in a pharmaceutically acceptable carrier and a container suitable for delivery of the composition by way of a parenteral delivery device. In some embodiments, the parenteral delivery device is an intramyocardial administration device. Instruments of containment are those that can be used to deliver, place, attach, or insert the ephrin into the myocardium, for example, a intramyocardial device for intramyocardial delivery of the ephrin to the subject. Such containers include, but are not limited to, vials, ampoules, tubes, capsules, bottles, syringes, and bags.

The ephrins described above can be formulated for administration in accordance with known pharmacy techniques. See, e.g., Remington, *The Science and Practice of Pharmacy* 20th Edition, Lippincott Williams & White, Baltimore, Md. (2000). In the manufacture of a pharmaceutical composition according to the present invention, the active agent (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier can be a solid or a liquid, or both, and is preferably formulated with the compound as a unit-dose formulation, for example, a tablet, which can contain from 0.01% or 0.5% to 95% or 99%, or any value between 0.01% and 99%, by weight of the active compound. One or more active compounds can be incorporated in the compositions of the invention, which can be prepared by any of the well-known techniques of pharmacy, comprising admixing the components, optionally including one or more accessory ingredients. Moreover, the carrier can be preservative free.

The formulations of the present invention can include those suitable for oral, rectal, topical, inhalation (e.g., via an aerosol) buccal (e.g., sub-lingual), vaginal, topical (i.e., both skin and mucosal surfaces, including airway surfaces), transdermal administration and parenteral or infusion (e.g., subcutaneous, intramuscular, intradermal, intraarticular, intrapleural, intraperitoneal, intrathecal, intracerebral, intracranially, intramyocardial, intraarterial or intravenous), although the most suitable route in any given case will depend on the nature and severity of the condition being treated and on the nature of the particular active compound which is being used.

Particular routes of parenteral administration include intravenous, intraarterial, intramyocardial injection, controlled, delayed release (implantable devices such as implanted infusion devices or pumps, for example, osmotic pumps, or using nanoparticles or other bioengineered materials and/or cells for sustained release.

Formulations suitable for oral administration can be presented in discrete units, such as capsules, cachets, lozenges, or tablets, each containing a predetermined amount of the active agent; as a powder or granules; as a solution or a suspension in an aqueous or non-aqueous liquid; or as an oil-in-water or water-in-oil emulsion. Such formulations can be prepared by any suitable method of pharmacy which includes bringing into association the active agent and a suitable carrier (which can contain one or more accessory ingredients as noted above). In general, the formulations of the invention are prepared by uniformly and intimately admixing the active agent with a liquid or finely divided solid carrier, or both, and then, if necessary, shaping the resulting mixture. For example, a tablet can be prepared by compressing or molding a powder or granules containing the active agent, optionally with one or more accessory ingredients. Compressed tablets can be prepared by compressing, in a suitable machine, the agent in a free-flowing form, such as a powder or granules optionally mixed with a binder, lubricant, inert diluent, and/or surface active/dispersing agent(s). Molded tablets can be made by molding, in a suitable machine, the powdered agent moistened with an inert liquid binder.

Formulations of the present invention suitable for parenteral administration comprise sterile aqueous and non-aqueous injection solutions of the active agent, which preparations are preferably isotonic with the blood of the intended recipient. These preparations can contain, buffers and solutes which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions and suspensions can be prepared from sterile powders, granules and tablets of the kind previously described.

For example, in some embodiments of the present invention, there is provided an injectable, stable, sterile composition comprising an active agent, or a salt thereof, in a unit dosage form in a sealed container. The agent or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the agent or salt. When the agent or salt is substantially water-insoluble, a sufficient amount of emulsifying agent which is physiologically acceptable can be employed in sufficient quantity to emulsify the agent or salt in an aqueous carrier. Non-limiting examples of agents that contribute to the pharmaceutical acceptability of the compositions of the present invention include normal saline, phosphatidyl choline, and glucose. In some embodiments, the pharmaceutically acceptable carrier can be normal saline. In other embodiments, the pharmaceutically acceptable carrier can be normal saline with up to 0.0, 0.01, 0.02, 0.03, 0.04, 0.05, 0.06, 0.07, 0.08, 0.09, 1.0, 2.0, 3.0, 4.0, 5.0, 6.0, 7.0, 8.0, 9.0, 10, 11, 12, 13, 14, 15, 16, 17, 18, 19, and 20%, and any value between 0.01% and 20%, glucose.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3(6)318 (1986)) and typically take the form of an optionally buffered aqueous solution of the active agent. Suitable formulations comprise citrate or bis\tris buffer (pH 6) or ethanol/water and contain from 0.1 to 0.2M active ingredient.

Further, the present invention provides liposomal formulations of the agents disclosed herein and salts thereof. The technology for forming liposomal suspensions is well known in the art. When the agent or salt thereof is an aqueous-soluble salt, using conventional liposome technology, the same can be incorporated into lipid vesicles. In such an instance, due to the water solubility of the agent or salt, the agent or salt will be substantially entrained within the hydrophilic center or core of the liposomes. The lipid layer employed can be of any conventional composition and can either contain cholesterol or can be cholesterol-free. When the agent or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the agents disclosed herein or salts thereof, can be lyophilized to produce a lyophilizate which can be reconstituted with a pharmaceutically acceptable carrier, such as water, to regenerate a liposomal suspension.

In addition to active agents or their salts, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the formulation is placed in a vial designed for multidose use. The pharmaceutical compositions of the present invention can be lyophilized using techniques well known in the art.

In particular embodiments, the ephrin is administered via intramyocardial injection. In this instance, the needle may be inserted into the left ventricle above and to the right of the site of coronary ligation. It is advanced toward the border zone of infarcted to non-infarcted tissue, where the protein is then delivered and when the "bleb" that is formed dissipates, the needle may be slowly withdrawn.

In other embodiments, the ephrin is administered via single or repetitive intracoronary, intravenous, subcutaneous, or intraperitoneal route, which may be performed anytime during or after the injury or when the occlusion is removed and coronary flow is restored.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes, and for drug screening and drug development purposes.

Suitable subjects additionally include subjects who are at risk for cardiovascular disease or have cardiovascular disease, those who are at risk for myocardial infarction or have suffered a myocardial infarction and/or those who are at risk for myocardial injury or have experienced myocardial injury including those suffering from or at risk for acute coronary events and those suffering from more long-term coronary disease such as congestive heart failure.

The present invention will now be described with reference to the following examples. It should be appreciated that these examples are for the purposes of illustrating aspects of the present invention, and do not limit the scope of the invention as defined by the claims.

EXAMPLE 1

Methods

All procedures were approved by the East Carolina University Institutional Animal Care and Use Committee and the investigation conforms to the *Guide for the Care and Use of Laboratory Animals* published by the US National Institutes of Health (NIH Publication No. 85-23, revised 1996).

Animals

Six week old B6/1295 breeder pairs were obtained from Jackson Laboratories (Bar Harbor, Me.) to establish an in-house colony (strain #101045). Animals were housed in 12-12 light/dark cycle conditions and received food and water ad libitum.

Surgical Procedure

Male 8-10 week old mice (22-28 g) were anesthetized (20 µl/g Avertin® (tribromoethanol) i.p.), intubated, and mechanically ventilated. The left anterior descending (LAD) coronary artery was permanently ligated using 8-0 suture. Sham controls in which the suture was pulled through the heart but not ligated, and either IgG-Fc or ephrinA1-Fc was injected, were done to ensure that there was no injury caused by the injection (data not shown). Infarction was confirmed by blanching of the myocardium distal to the site of ligation. Following coronary occlusion, using a Hamilton syringe with a sterile 30 gauge needle, animals received a single intramyocardial injection of either 6 µg IgG-Fc (R&D #110-HG), or 6 µg ephrinA1-Fc (Sigma #E9902) resuspended in 6 µl sterile PBS at the peri-infarct zone. This dose was chosen based on prior studies showing effective doses of intramyocardial injections of Tβ4 (Bock-Marquette et al., 2004) and intraperitoneal injection of ephrinB2-Fc (Mansson-Broberg et al., 2008). Additionally, this dose is within the therapeutic range (for humans) of the maximum recommended therapeutic dose (MRTD) 0.00001 to 1000 mg/kg-bw/day, as defined by the FDA (Contrera et al., 2004). Taking into account heart weight, potential for efflux of the protein from the heart via the injection site, and that an average mouse left ventricle weighs approximately 150 mg, injecting 6 µg of protein intramyocardially is within this range (approximately 40 mg/kg). The investigator performing the surgery was blinded as to the treatment, which were randomized by another investigator. Once the animals recovered, they were returned to the vivarium. The surgical procedure is described in more detail elsewhere (Virag & Murry, 2003; Virag et al., 2010).

Four days after surgery, mice were given a 0.5 ml i.p. injection of 5-bromodeoxyuridine (BrdU, 5 mg/ml) to label proliferating endothelial cells and anesthetized 1 hour later with an i.p. injection of 0.1 mL pentobarbital (390 mg/mL) (Virag & Murry, 2003). The heart was arrested in diastole using cold KCl (30 mM), excised, rinsed in PBS, and immersed in zinc fixative with a segment of small intestine (used as a positive control for $BrdU^+$ proliferating cells). Hearts were sectioned transversely into 4 slices of equal thickness and were processed and embedded in paraffin. Routine histological (hematoxylin and eosin) procedures and immunostaining were performed using 5 µm sections, as described below (Virag & Murry, 2003).

EphrinA1-Fc Distribution in the Myocardium

To determine the distribution pattern and duration of persistence of ephrinA1-Fc in the nonreperfused myocardium, an anti-human IgG-Fc was used to immunolocalize the ephrinA1 chimera in hearts at 30 min, 4 hr, and 24 h post-injection (n=3 per group). A representative image (FIG. 1) shows prominent epicardial and transmural staining at 30 min. Light staining was observed in 2 of 3 hearts at 4 hr but none was observed at 24 hr or 4 days post injection, saline injected hearts, or in tissues incubated without the primary antibody (data not shown).

Histology and Morphometry

Images of four haematoxylin and eosin-stained sections per heart were taken at 20× magnification using a DP70 digital camera. Two sections of infarct, approximately 1 mm apart (apical and closer to the ligation site) and two sections of base in non-infarcted regions, also 1 mm apart, were used. Scion imaging software (Scion Corporation, Frederick, Md., USA) was used to trace the cross sectional area of the left ventricular wall and chamber, as well as the infarct zone (necrosis+granulation tissue) and necrosis. Measurements from three to four complete, transverse profiles per heart were averaged. Septal and free wall thicknesses were also measured using the average of three radial measures in each of two sections containing infarct. The investigator was blinded as to the treatment while obtaining morphometric measurements. After determining that there was no significant difference between IgG-Fc-treated hearts and standard 4 day-infarcted hearts without any injection, we used 4 day MI hearts for protein and RNA analysis, and this experimental group is labelled as MI rather than IgG-Fc, which was the group used for histological and immunohistochemical analysis.

Immunostaining

Tissue sections were deparaffinized in xylene and endogenous peroxidases quenched with 3% $H_2O_2$ in methanol. Slides were rinsed in PBS and incubated with anti-ephrinA1 (Zymed #34-3300), CD45 (PharMingen, #550539; 1:2000) for leukocytes, Ly6G (PharMingen #550291) for neutrophils, or CD31 (PharMingen #553371) and anti-BrdU (Roche #11585860001) for proliferating endothelial cells. Slides were incubated with appropriate biotinylated secondary antibodies and then with Avidin Biotin Complex (Vector Labs PK-6100). The reaction product was visualized with DAB (Vector, SK-4100), counterstained with methyl green, dehydrated in xylene, and slides were coverslipped. For the ephrinA1 staining, a second antibody, anti-ephrinA1 (Santa Cruz, # sc-911) was used to verify consistent staining pattern. Negative controls were performed in the same manner but without a primary antibody. For mast cell staining, slides were sent to Histo-Scientific Research Laboratories (Mount Jackson, Va.) for pinacyanol erthrosinate staining to identify mast cells (Murray et al., 2004). Leukocyte, neutrophil, and mast cell density was measured in 3 fields per section of 2 sections of infarcted heart at 400×. Results were expressed as the number of cells per 0.1 $mm^2$. For proliferating endothelial cells ($BrdU^+$+$CD31^+$), numbers are expressed as a percentage of 1000 endothelial cells ($CD31^+$ only).

Cardiac Troponin I (cTnI) Measurements

Approximately 50-100 µl of whole blood was collected from mice pre-surgery and at the time of euthanasia by a submandibular bleed, stored in lithium heparin coated tubes on a rocker to prevent clotting, and analyzed within 30 minutes of collection on an i-STAT® Handheld Clinical Analyzer with cTnI cartridges (Abbott Labs). Values are expressed as nanograms per milliliter.

Protein Isolation

Whole left ventricles (LV) were snap frozen in liquid nitrogen at the time of collection, and stored at −80° C. until use. The whole LV was homogenized in a lysis buffer containing 50 mM hepes, 10 mM EDTA, 100 mM NaF, 50 mM Na pyrophosphate, and 1% each of protease and phosphatase inhibitors. Protein was quantified using the Bradford Assay.

Western Blotting

Western blotting was performed on a 4-12% gradient Bis-Tris gel (BioRad) in 1× MOPS running buffer. 50 ug of sample was loaded per well, and the gel was run for 1 hour at 155V, and transferred for 55 minutes (for ephrinA1, BAG-1 and GAPDH) or 1 hr 30 min (for cleaved PARP, AKT, and pAKT) onto pure nitrocellulose membranes (BioRad). The membrane was incubated with one of the following antibodies: cleaved PARP (89 kDa; Cell Signaling #9544; 1:1000), ephrinA1 (28 kDa; Santa Cruz, sc-911; 1:100), AKT (Cell Signaling #4691, 1:1000), phospho-AKT (Cell Signaling #4060, 1:2000), and GAPDH (37 kDa; Millipore® #MAB374; 1:100), followed by appropriate secondary antibodies. EphrinA1 and cleaved PARP were run on the same membrane, which was cut horizontally at 50 kDa, with the bottom half of the membrane used for the ephrinA1 blot, and the top half used for the cleaved PARP blot. The ephrinA1 blot was then stripped/reprobed for anti-GAPDH to confirm equal protein loading. All blots were detected with Amersham ECL Advance (GE Healthcare #RPN2135) and imaged on a Typhoon Imager. Densitometry was performed using Image J software and the intensity of each protein was normalized to GAPDH. In the case of pAKT/AKT, the amount of phosphorylated AKT protein was normalized to total AKT.

RNA Extraction and Real-Time RT-PCR

The TRIzol® method was used for RNA isolation, followed by the Quiagen RNeasy® kit for additional purification. cDNA was synthesized using a high capacity cDNA kit. Real-time RT-PCR was conducted on an Applied Biosystems® thermocycler. A reaction mixture of 10 µL containing 100 ng RNA was amplified using recommended conditions for TaqMan® primers provided by Applied Biosciences. TaqMan primers and probes were obtained from Applied Biosciences (EphrinA1: Mm00438660_m1), EphA1: Mm00445804_m1, EphA2: Mm00438726_m1, EphA3: Mm00580743_m1, EphA4: Mm00433056_m1, EphA5: Mm00433074_m1, EphA6: Mm00433094_m1, EphA7: Mm00833876_m1, GAPDH: Mm99999915_g1). In each experiment, fluorescence data were analyzed using the ΔΔCT method. Gene expression was normalized to the housekeeping gene GAPDH. No Template Controls (NTC) were included in each experiment, and all samples were run in triplicate.

Statistics

Student t-tests were used to test statistical significance between 4 day MI and ephrinA1-Fc-treated MI for RT-PCR, relative infarct size, and necrosis. ANOVAs and student Newman-Keuls post-hoc analyses were used to determine differences between control, 4 day MI, and ephrinA1-Fc-treated MI for cTnI, inflammatory cell density, chamber area, and left ventricular free wall thickness. The number of hearts analyzed for each endpoint and significance levels have been specified for each experiment in reference to the figures. Four animals were excluded from all experiments: two from each group, based on suboptimal cTnI and/or overall health of the animals.

EXAMPLE 2

Figure 2:
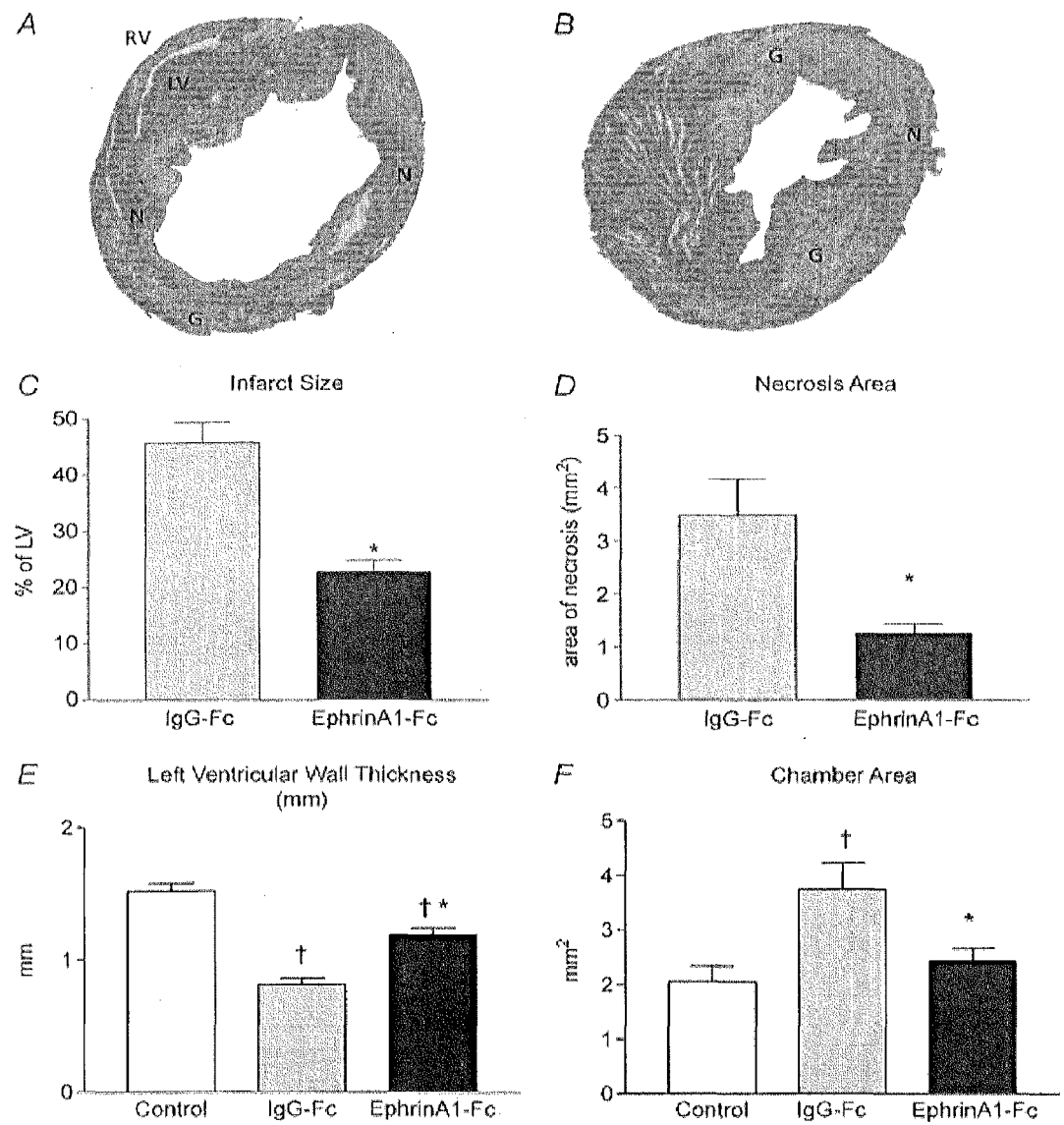
FIG. 2. EphrinA1-Fc administration reduces infarct size, chamber dilation, necrosis, and thinning of the left ventricular free wall. Representative histological images shown are of vehicle-treated (A) and ephrinA1-Fc-treated (B) hearts four days post-MI. There was a 50% reduction in infarct size (C), 64% less necrosis (D), 35% less chamber dilation (E), and 32% less thinning of the left ventricular free wall (F). n=7 control, n=9 IgG-Fc, n=9 ephrinA1-Fc, P<0.05: † different from control, * different from IgG-Fc. LV: Left Ventricle; RV: Right Ventricle; N: Necrosis; G: Granulation tissue.

EphrinA1-Fc Reduces Infarct Size, Necrosis, Chamber Dilation, and Left Ventricular Free Wall Thinning EphrinA1-Fc or IgG-Fc was injected into the border zone of the infarct immediately after coronary ligation. Four days after surgery, tissue was collected and either fixed for histology and immunohistochemistry, or frozen for RNA and protein isolation. Overall survival for this study was 70%, and there was no difference in survival between experimental groups. Histological staining and morphometric analyses (FIG. 2) show a 50% reduction in the size of the infarct (expressed as a percent of the left ventricle), 64% less necrotic area, a 35% reduction in chamber dilation, and 32% less thinning of the infarcted left ventricular free wall. There was no significant difference in chamber area between uninjured control hearts and those treated with ephrinA1-Fc at day 4 post-MI.

EXAMPLE 3

Cardiac Troponin I Levels Reduced with ephrinA1-Fc Administration

Figure 3:
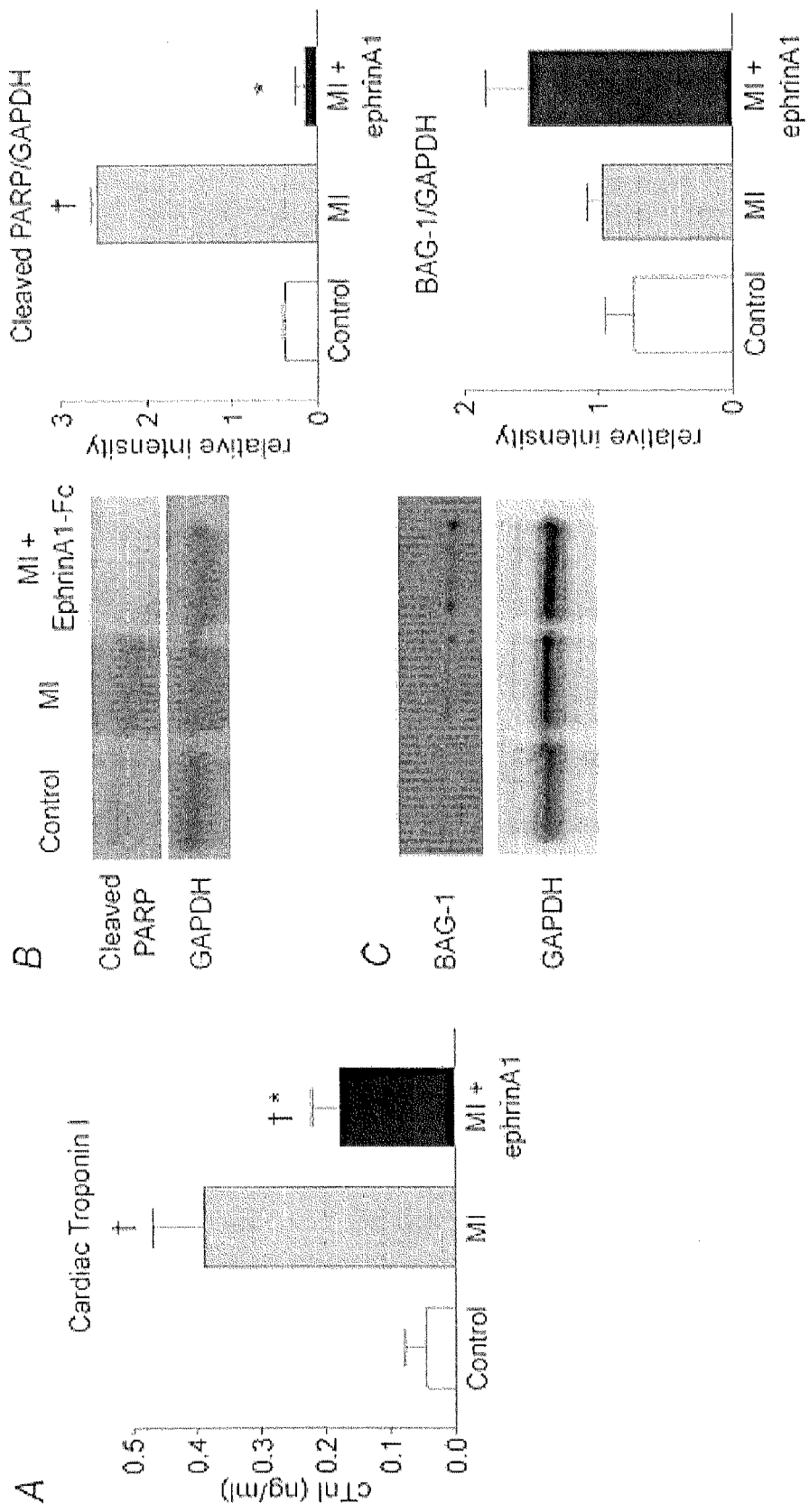
FIG. 3. Intramyocardial ephrinA1-Fc administration reduces tissue injury. Administration of ephrinA1-Fc resulted in a 54% reduction in cTnI serum levels 4 days after MI (A), (n=8 control, n=13 vehicle, n=11 ephrinA1-Fc). Cleaved PARP expression was reduced with ephrinA1-Fc administration (B). BAG-1 protein (C) increased with ephrinA1-Fc administration by 36% when normalized to GAPDH. P<0.05: j different from control, * different from MI.

Serum cTnI levels were measured prior to surgery and at the time of euthanasia (four days post-MI) in the same animals. There was an 89% increase in cTnI levels following MI in vehicle treated hearts. However, cTnI levels in ephrinA1-Fc treated hearts were 54% lower than those from vehicle treated animals (FIG. 3A). There was no significant difference between pre-surgery levels and those of ephrinA1-Fc treated animals four days post-surgery.

EXAMPLE 4

EphrinA1-Fc Treated Hearts Show Diminished cleaved PARP Expression and Increased BAG-1 Expression Cleaved PARP, the main target of caspase-3 and an indicator of increased apoptosis (Nicholson et al., 1995; Tewari et al., 1995; Oliver et al., 1998), increased by approximately 88% in response to MI, but diminished with ephrinA1-Fc treatment (FIG. 3B) below control levels. Although we did not observe a change in the level of Bcl-2 protein expression with ephrinA1-Fc treatment (data not shown), we did observe a change in Bcl-2-associated athanogene-1 (BAG-1). BAG-1 is a protein that enhances the anti-apoptotic effects of Bcl-2 and has also been identified as a cardioprotective protein through interactions with heat shock proteins (Doong et al., 2002; Townsend et al., 2004). EphrinA1-Fc administration upregulated the expression of the BAG-1 protein by approximately 54% (FIG. 3C).

EXAMPLE 5

Figure 4:
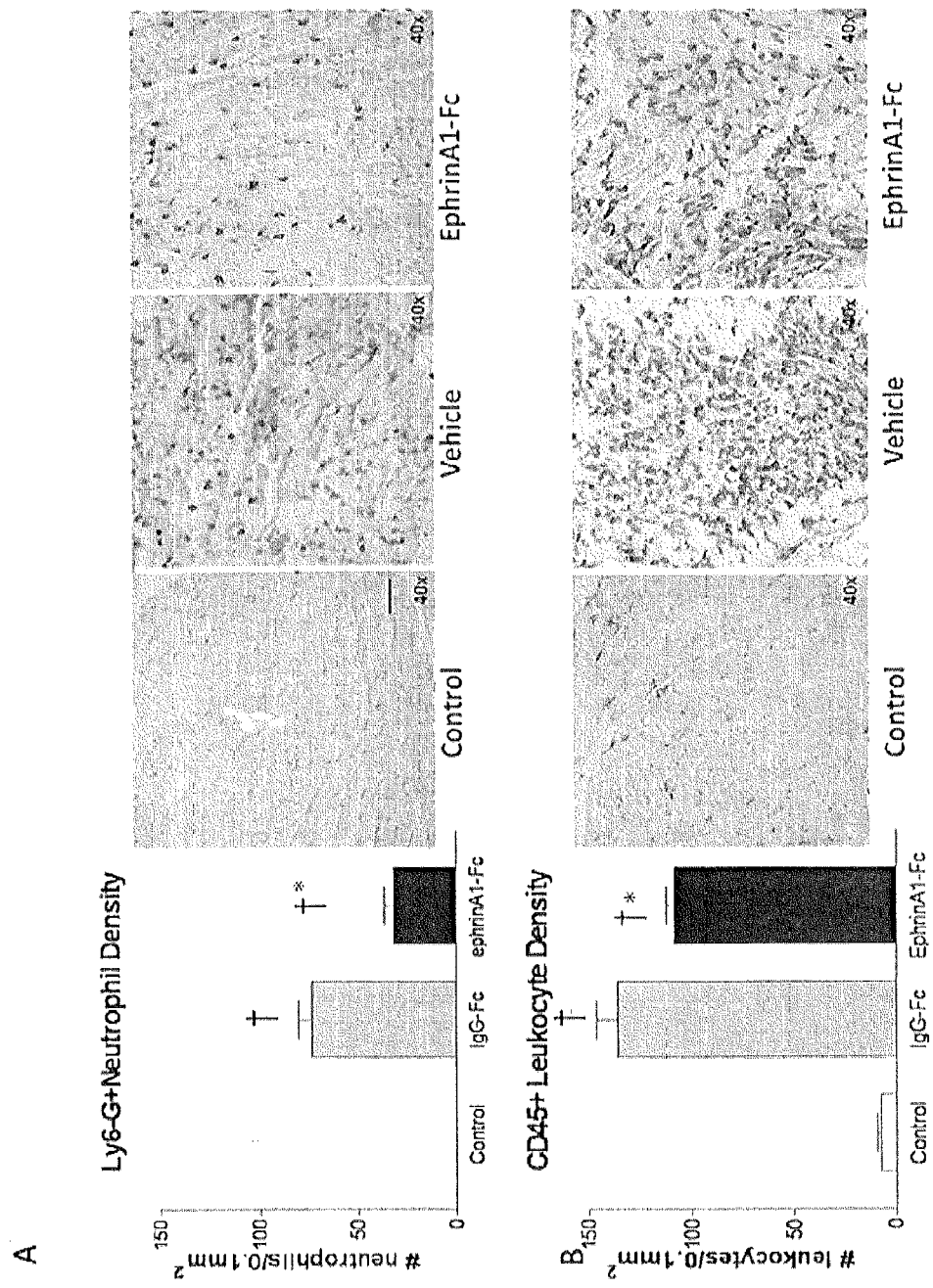
FIG. 4. EphrinA1-Fc reduces inflammatory cell infiltration. EphrinA1-Fc administration significantly reduced infiltration of neutrophils (A) and leukocytes (B) at 4 days. n=3 control, n=9 IgG-Fc, n=9 ephrinA1-Fc. P<0.05: † different from control, * different from MI. Representative images of Ly6G+ neutrophil infiltration (top panels) and CD45+ pan-leukocyte infiltration (bottom panels) are shown in control (left), vehicle-treated (middle) and ephrinA1-Fc-treated (right) hearts. Scale bar in A (Control) represents 50 µm.

EphrinA1-Fc Treatment Reduces Inflammatory Cell Infiltration to Infarcted Myocardium Results indicate a 57% reduction in neutrophil density (FIG. 4A) and a 21% reduction in leukocyte density in ephrinA1-Fc-treated versus IgG-Fc-treated hearts at 4 days post-MI (FIG. 4B), indicating ephrinA1-Fc attenuates the inflammatory response. No statistical differences were observed in the numbers of mast cells between ephrinA1-Fc and vehicle treated hearts, with only a few (1-6 per section of LV) mast cells per heart (data not shown).

EXAMPLE 6

EphrinA1-Fc Treatment Does not Influence the Angiogenic Response to MI

No differences were seen in endothelial cell proliferation (5.0±1% vs. 6.1±1.3%; n=3 vehicle, n=5 ephrinA1-Fc) or capillary density (111±26.4 vs. 111±26.0 vessels per 40× high power field, n=4 per group) between vehicle- and ephrinA1-Fc-treated hearts, respectively.

EXAMPLE 7

EphrinA1 and EphA Receptor Gene Expression in Response to EphrinA1-Fc Treatment

Figure 5:
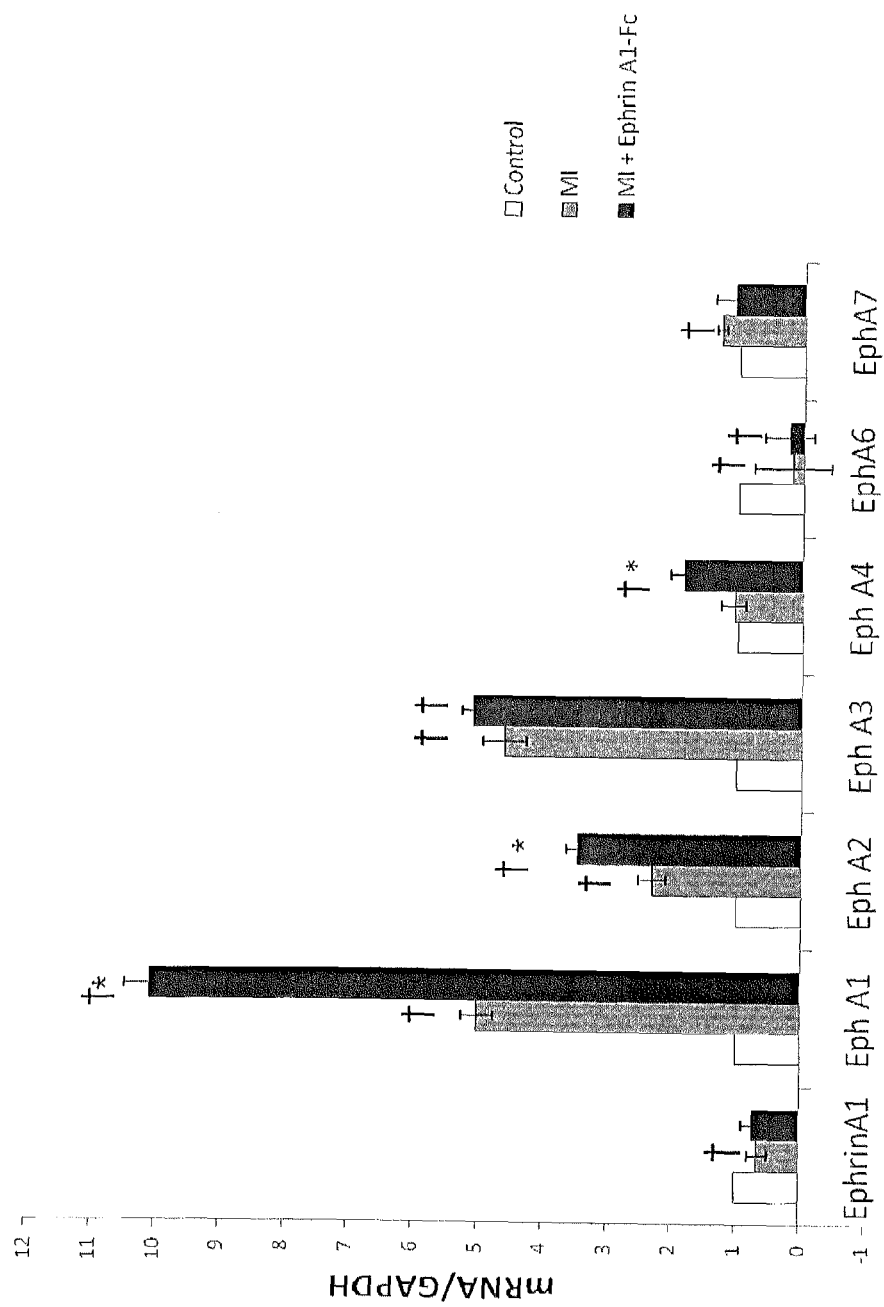
FIG. 5. Altered gene expression of ephrinA1 and EphA receptors in response to MI and MI+ephrinA1-Fc. Following MI, ephrinA1 gene expression was significantly reduced (grey bars), and remained relatively unchanged in response to ephrinA1-Fc administration (black bars). Receptors A1, A2, A3 and A7 were significantly upregulated in response to MI, by 5-fold, 2-fold, 5-fold and 28%, respectively, while EphA4 remained unchanged. EphA6 was detected in control hearts but dropped significantly following MI, and expression was not recovered with ephrinA1-Fc administration. In response to ephrinA1-Fc administration, receptors A1 and A2 were further upregulated, by approximately 2-fold each, and A4 was also upregulated by almost 2-fold. Values were calculated using the Ct method, normalized to GAPDH, and presented here as fold changes relative to uninjured control (white bars), n=8 control, n=8 MI, n=8 ephrinA1-Fc. P<0.05: † different from control, * different from MI.

EphrinA1 gene expression was quantified using qRT-PCR. mRNA levels decrease significantly by 35% following MI, and remain unchanged with ephrinA1-Fc treatment (FIG. 5). Of the eight receptors, EphA1, A2, A3, and A7 were all significantly upregulated four days after MI (5-fold, 2-fold, 5-fold, and 28%, respectively); EphA1 andA2 were further upregulated with ephrinA1-Fc treatment (10-fold and 3-fold, respectively, from control). Despite not changing in response to MI, EphA4 was significantly upregulated 2-fold with ephrinA1-Fc treatment. EphA6 was detected in control hearts, but significantly decreased in response to MI, and expression in the ephrinA1-Fc-treated group was unchanged relative to the untreated MI group (FIG. 5). Ligands ephrinA2-A5 and EphrinB3 (the only B ligand known to bind to an EphA receptor, specifically, EphA4) were also detected in the heart, but their expression did not change in response to MI or ephrinA1-Fc administration (data not shown).

EXAMPLE 8

Endogenous EphrinA1 Tissue Expression Pattern post-MI and in Response to EphrinA1-Fc Treatment In uninjured control hearts, endogenous ephrinA1 protein expression appeared to be expressed at a low, basal level on cardiac myocytes throughout the myocardium (FIGS. 6A and D). Four days after MI, ephrinA1 protein expression was expressed in cardiomyocytes throughout the uninjured regions of the hearts and was also localized to the spared cardiac myocytes on both the epicardial and endocardial surfaces of the myocardium, at the border zones of the infarct (FIGS. 6B and 6E). In the ephrinA 1-Fc-treated hearts at 4 days post-MI, endogenous ephrinA1 protein expression appeared to be localized not only to the cardiomyocytes, but also to infiltrating granulation tissue cells throughout the infarct zone (FIGS. 6C and F).

EXAMPLE 9

EphrinA1 Protein Expression post-MI and in Response to EphrinA1-Fc Treatment

Figure 6G:
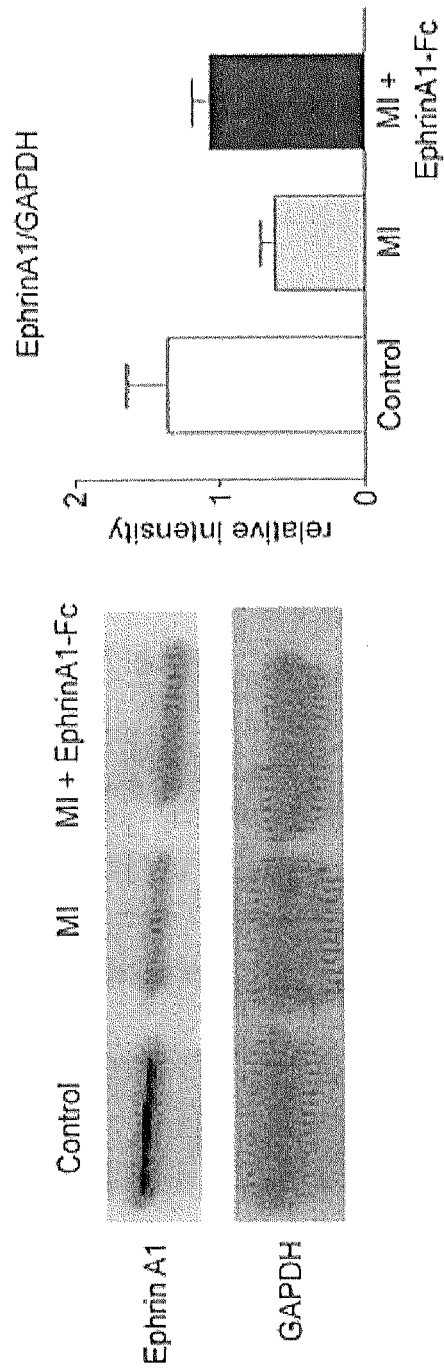
FIG. 6. EphrinA1 protein distribution in the myocardium. Representative immunostaining for ephrinA1 protein showed a low basal expression of ephrinA1 in cardiomyocytes of control hearts (A and D), intense staining in endo- and epicardial myocytes following 4 days non reperfused MI (B and E), and more intense staining in myocytes as well as numerous granulation tissue cells in the infarct zone following ephrinA1-Fc treatment at 4 days post-MI (C and F). EphrinA1 total protein expression (G) was reduced by 50% in response to MI, but only reduced 36% in response to ephrinA1-Fc administration (normalized to GAPDH). Scale bars: 100 µm in A, 20 µm in D.

Western blotting was used to quantify endogenous ephrinA1 expression. Since anti-IgG-Fc immunostaining (FIG. 1) shows that expression of the chimeric protein is greatly reduced by 4 hours post-injection, and completely abolished by 24 hours, ephrinA1 protein expression detected at 4 days is only the endogenous protein. In addition, the molecular weight for the chimera is 42 kDa (not observed), vs. 28 kDa for the native protein. Endogenous ephrinA1 protein expression decreased 50% with MI, but was only diminished by approximately 36% with ephrinA1-Fc treatment (FIG. 6G).

EXAMPLE 10

EphrinA1-Fc Administration Increases pAKT/total AKT Ratio

Figure 7:
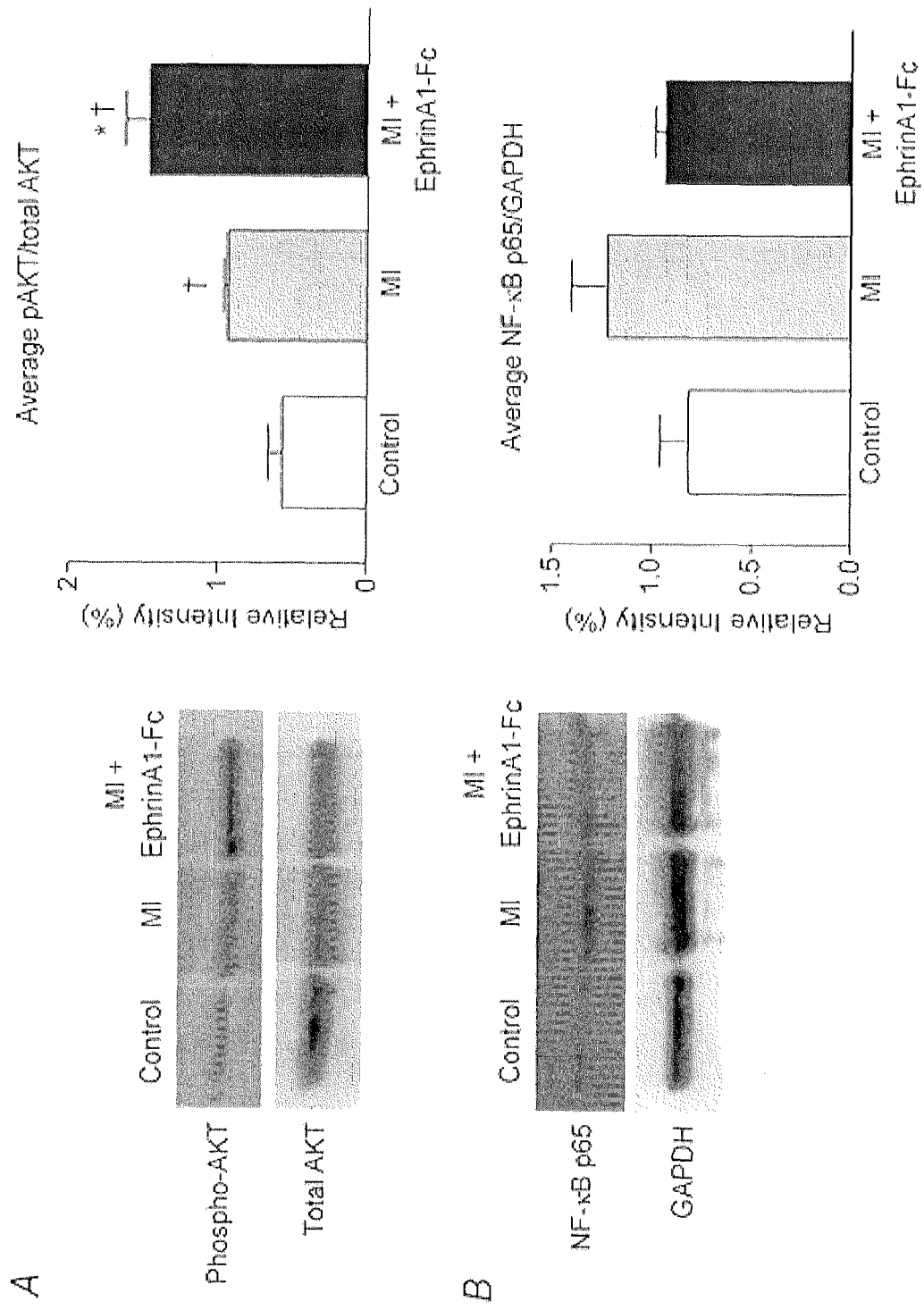
FIG. 7. EphrinA1-Fc increases pAKT/AKT. (A), representative blot of phosphorylated and total AKT, with the average densitometric analysis of three repeated blots. n=3 control, n=3 MI, n=3 ephrinA1-Fc. P<0.05: † different from control, *different from MI. (B), representative blot of NF-κB p65 protein expression, normalized to GAPDH. n=3 control, n=3 MI, n=3 ephrinA1-Fc.

Total and phosphorylated AKT protein was measured using western blotting. While total AKT remained unchanged in the three groups (Control, 4 day MI, and EphrinA1-Fc treated), phosphorylated AKT levels increased with EphrinA1-Fc treatment following MI (FIG. 7A). The pAKT/AKT ratio was significantly higher in the MI group compared to control, and further increased in ephrinA1-Fc-treated hearts compared to both control and MI.

EXAMPLE 11

NF-κB p65 Protein Reduced with EphrinA1-fc Administration

Protein levels of nuclear factor κ light-chain enhancer of activated B cells (NF-κB) were measured with Western blotting, and a trend for reduced expression of this immune-modulatory protein with ephrinA1-Fc administration was observed (FIG. 7B).

EXAMPLE 12

Comparison of Infarct Size in Reperfused Versus Nonreperfused Myocardium

Currently, reperfusion is the only treatment known to improve longevity in patients with acute myocardial infarction. Reperfusion can accelerate phagocytic resorption of necrotic myocardium and expedite its replacement with granulation tissue, thus reducing remodeling. However, this therapy is generally applied within 6 hours following the occlusive event in order to salvage any of the highly ischemia-sensitive myocardial tissue. The therapeutic efficacy of reperfusion generally declines exponentially within hours of occlusion onset, causes additional oxidative stress and, if flow is not restored, infarct injury proceeds and accelerates, with poor long-term prognosis.

This experiment is designed to compare the infarct size in reperfused versus nonreperfused myocardium following 1) sham operation, 2) intramyocardial IgG-Fc administration, 3) intramyocardial ephrinA1-Fc injection, and 4) an intravenous (i.v.) injection of ephrinA1-Fc. The following table illustrates the groups and number of mice needed for each (assuming at least 85% survival).

Experiment #1:

| Experimental Groups | Untreated sham | 6 µg IgG-Fc intramyocardial | 6 µg ephrinA1-Fc intramyocardial | 20 µg ephrinA1-Fc i.v. |
|---|---|---|---|---|
| 4 day nonreperfused | 4* | 4* | 4* | 12 |
| 30 min I/4 day reperfusion | 12 | 12 | 12 | 12 |

*additions to existing data sets (Dries et al. (2011) *J. Physiol.* 589: 1725-1740)

Baseline serum troponin I (TnI) is measured prior to surgery and again prior to sacrifice as an index of myocardial damage. Similarly, baseline cardiac function (fractional shortening, ejection fraction, LV mass, and systolic and diastolic dimensions) of each animal prior to surgery and again prior to sacrifice is performed using echocardiographic analyses. In control animals and at the time of sacrifice of the experimental animals, in vivo pressure-volume analysis (HR, ESBP, EDBP, ESV, EDV, SV, EF+/−dP/dt) is performed via catheterization using a 1.4 Fr conductance catheter. Animals are given an intraperitoneal injection of isoproterenol (0.25 mg/kg) to assess their contractile reserve in response to acute cardiovascular stress. ECG recordings are obtained and arrhythmia scores are be generated. Histologic examination and morphometric analyses are be performed to measure differences in infarct size, composition (necrosis and granulation tissue), and ventricular dimensions (septal and free wall thickness).

EXAMPLE 13

Presence of EphrinA1-Fc in the Myocardium Relative to the Area at Risk During Intravenous Administration Compared to Intramyocardial Administration Immunohistochemistry is used to evaluate the presence and distribution of ephrinA1-Fc in the heart relative to the area at risk (TTC staining) when administered intravenously compared to intramyocardial injection. EphrinA1-Fc is administered intramyocardially or with an i.v. injection at the time of ligation in mice and the table below describes the experimental groups and numbers of mice in each group.

| Experimental Groups | 6 µg ephrinA1-Fc intramyocardial | 20 µg ephrinA1-Fc i.v. |
|---|---|---|
| 2 hr nonreperfused | 10 | 10 |
| 30 min I/2 hr reperfusion | 10 | 10 |

The foregoing is illustrative of the present invention, and is not to be construed as limiting thereof. The invention is defined by the following claims, with equivalents of the claims to be included therein.

REFERENCES

Aasheim H C, Delabie J & Finne E F. (2005). Ephrin-A1 binding to CD4+ T lymphocytes stimulates migration and induces tyrosine phosphorylation of PYK2. *Blood* 105, 2869-2876.

Abbate A, Biondi-Zoccai G G, Van Tassell B W & Baldi A. (2009). Cellular preservation therapy in acute myocardial infarction. *Am J Physiol Heart Circ Physiol* 296, H563-565.

Arvanitis D & Davy A. (2008). Eph/ephrin signaling: networks. *Genes Dev* 22, 416-429.

Bartunek J, Vanderheyden M, Hill J & Terzic A. (2010). Cells as biologics for cardiac repair in ischaemic heart failure. *Heart* 96, 792-800.

Bock-Marquette I, Saxena A, White M D, Dimaio J M & Srivastava D. (2004). Thymosin beta4 activates integrin-linked kinase and promotes cardiac cell migration, survival and cardiac repair. *Nature* 432, 466-472.

Bodor G S, Porterfield D, Voss E M, Smith S & Apple F S. (1995). Cardiac troponin-I is not expressed in fetal and healthy or diseased adult human skeletal muscle tissue. *Clin Chem* 41, 1710-1715.

Brantley-Sieders D, Schmidt S, Parker M & Chen J. (2004). Eph receptor tyrosine kinases in tumor and tumor microenvironment. *Curr Pharm Des* 10, 3431-3442.

Brantley-Sieders D M, Fang W B, Hwang Y, Hicks D & Chen J. (2006). Ephrin-A1 facilitates mammary tumor metastasis through an angiogenesis-dependent mechanism mediated by EphA receptor and vascular endothelial growth factor in mice. *Cancer Res* 66, 10315-10324.

Braunwald E, Antman E M, Beasley J W, Califf R M, Cheitlin M D, Hochman J S, Jones R H, Kereiakes D, Kupersmith J, Levin T N, Pepine C J, Schaeffer J W, Smith E E, 3rd, Steward D E, Theroux P, Gibbons R J, Alpert J S, Faxon D P, Fuster V, Gregoratos G, Hiratzka L F, Jacobs A K & Smith S C, Jr. (2002). ACC/AHA guideline update for the management of patients with unstable angina and non-ST-segment elevation myocardial infarction—2002: summary article: a report of the American College of Cardiology/American Heart Association Task Force on Practice Guidelines (Committee on the Management of Patients With Unstable Angina). *Circulation* 106, 1893-1900.

Bruckner K, Pasquale E B & Klein R. (1997). Tyrosine phosphorylation of transmembrane ligands for Eph receptors. *Science* 275, 1640-1643.

Chapelle J P. (1999). Cardiac troponin I and troponin T: recent players in the field of myocardial markers. *Clin Chem Lab Med* 37, 11-20.

Chen G, Wang Y, Zhou M, Shi H, Yu Z, Zhu Y & Yu F. (2010). EphA1 receptor silencing by small interfering RNA has antiangiogenic and antitumor efficacy in hepatocellular carcinoma. *Oncol Rep* 23, 563-570.

Cheng N, Brantley D M & Chen J. (2002a). The ephrins and Eph receptors in angiogenesis. *Cytokine Growth Factor Rev* 13, 75-85.

Cheng N, Brantley D M, Liu H, Lin Q, Enriquez M, Gale N, Yancopoulos G, Cerretti D P, Daniel T O & Chen J. (2002b). Blockade of EphA receptor tyrosine kinase activation inhibits vascular endothelial cell growth factor-induced angiogenesis. *Mol Cancer Res* 1, 2-11.

Cheng W, Kajstura J, Nitahara J A, Li B, Reiss K, Liu Y, Clark W A, Krajewski S, Reed J C, Olivetti G & Anversa P. (1996). Programmed myocyte cell death affects the viable myocardium after infarction in rats. *Exp Cell Res* 226, 316-327.

Contrera J F, Matthews E J, Kruhlak N L & Benz R D. (2004). Estimating the safe starting dose in phase I clinical trials and no observed effect level based on QSAR modeling of the human maximum recommended daily dose. *Regul Toxicol Pharmacol* 40, 185-206.

Curato C, Slavic S, Dong J, Skorska A, Altarche-Xifro W, Miteva K, Kaschina E, Thiel A, Imboden H, Wang J, Steckelings U, Steinhoff G, Unger T & Li J. (2010). Identification of Noncytotoxic and IL-10-Producing CD8+AT2R+ T Cell Population in Response to Ischemic Heart Injury. *J Immunol* 185, 6286-6293.

Doong H, Vrailas A & Kohn E C. (2002). What's in the 'BAG'?—A functional domain analysis of the BAG-family proteins. *Cancer Lett* 188, 25-32.

Dorn G W, 2nd. (2009). Novel pharmacotherapies to abrogate postinfarction ventricular remodeling. *Nat Rev Cardiol* 6, 283-291.

Dorn G W, 2nd & Diwan A. (2008). The rationale for cardiomyocyte resuscitation in myocardial salvage. *J Mol Med* 86, 1085-1095.

Easty D J, Hill S P, Hsu M Y, Fallowfield M E, Florenes V A, Herlyn M & Bennett D C. (1999). Up-regulation of ephrin-A1 during melanoma progression. *Int J Cancer* 84, 494-501.

Edelberg J M, Lee S H, Kaur M, Tang L, Feirt N M, McCabe S, Bramwell O, Wong S C & Hong M K. (2002). Platelet-derived growth factor-AB limits the extent of myocardial infarction in a rat model: feasibility of restoring impaired angiogenic capacity in the aging heart. *Circulation* 105, 608-613.

Fishbein M C, Maclean D & Maroko P R. (1978). Experimental myocardial infarction in the rat: qualitative and quantitative changes during pathologic evolution. *Am J Pathol* 90, 57-70.

Frangogiannis N G. (2008). The immune system and cardiac repair. *Pharmacol Res* 58, 88-111

Frangogiannis N G, Smith C W & Entman M L. (2002). The inflammatory response in myocardial infarction. *Cardiovascular Research* 53, 31-47.

Freude B, Masters T N, Kostin S, Robicsek F & Schaper J. (1998). Cardiomyocyte apoptosis in acute and chronic conditions. *Basic Res Cardiol* 93, 85-89.

Fume C, Ricard J, Cabrera J R, Pays L, Bethea J R, Mehlen P & Liebl D J. (2009). EphrinB3 is an anti-apoptotic ligand that inhibits the dependence receptor functions of EphA4 receptors during adult neurogenesis. *Biochim Biophys Acta* 1793, 231-238.

Gaudron P, Eilles C, Kugler I & Ertl G. (1993). Progressive left ventricular dysfunction and remodeling after myocardial infarction. Potential mechanisms and early predictors. *Circulation* 87, 755-763.

Giaginis C, Tsourouflis G, Zizi-Serbetzoglou A, Kouraklis G, Chatzopoulou E, Dimakopoulou K & Theocharis S E. Clinical significance of ephrin (eph)-A1, -A2, -a4, -a5 and -a7 receptors in pancreatic ductal adenocarcinoma. *Pathol Oncol Res* 16, 267-276.

Goldstein S, Ali A S & Sabbah H. (1998). Ventricular remodeling. Mechanisms and prevention. *Cardiol Clin* 16, 623-632, vii-viii.

Gurusamy N, Lekli I, Gorbunov N V, Gherghiceanu M, Popescu L M & Das D K. (2009). Cardioprotection by adaptation to ischaemia augments autophagy in association with BAG-1 protein. *J Cell Mol Med* 13, 373-387.

Haider H, Jiang S, Idris N M & Ashraf M. (2008). IGF-1-overexpressing mesenchymal stem cells accelerate bone marrow stem cell mobilization via paracrine activation of SDF-1alpha/CXCR4 signaling to promote myocardial repair. *Circ Res* 103, 1300-1308.

Hausenloy D J & Yellon D M. (2006). Survival kinases in ischemic preconditioning and postconditioning. *Cardiovasc Res* 70, 240-253.

Hirai H, Maru Y, Hagiwara K, Nishida J & Takaku F. (1987). A novel putative tyrosine kinase receptor encoded by the eph gene. *Science* 238, 1717-1720.

Holen H L, Nustad K & Aasheim H C. (2010). Activation of EphA receptors on CD4+CD45RO+ memory cells stimulates migration. *J Leukoc Biol* 87, 1059-1068.

Holen H L, Shadidi M, Narvhus K, Kjosnes O, Tierens A & Aasheim H C. (2008). Signaling through ephrin-A ligand leads to activation of Src-family kinases, Akt phosphorylation, and inhibition of antigen receptor-induced apoptosis. *J Leukoc Biol* 84, 1183-1191.

Holmes J W, Borg T K & Covell J W. (2005). Structure and mechanics of healing myocardial infarcts. *Annu Rev Biomed Eng* 7, 223-253.

Hwang H & Kloner R A. (2010). Improving regenerating potential of the heart after myocardial infarction: factor-based approach. *Life Sci* 86, 461-472.

Iida H, Honda M, Kawai H F, Yamashita T, Shirota Y, Wang B C, Miao H & Kaneko S. (2005). Ephrin-A1 expression contributes to the malignant characteristics of {alpha}-fetoprotein producing hepatocellular carcinoma. *Gut* 54, 843-851.

Ivanov A I & Romanovsky A A. (2006). Putative dual role of ephrin-Eph receptor interactions in inflammation. *IUBMB Life* 58, 389-394.

Iwanaga K, Takano H, Ohtsuka M, Hasegawa H, Zou Y, Qin Y, Odaka K, Hiroshima K, Tadokoro H & Komuro I. (2004). Effects of G-CSF on cardiac remodeling after acute myocardial infarction in swine. *Biochem Biophys Res Commun* 325, 1353-1359.

Jaffe A S. (2005). Use of biomarkers in the emergency department and chest pain unit. *Cardiol Clin* 23, 453-465, vi.

Klein R. (2001). Excitatory Eph receptors and adhesive ephrin ligands. *Curr Opin Cell Biol* 13, 196-203.

Kullander K & Klein R. (2002). Mechanisms and functions of Eph and ephrin signalling. *Nat Rev Mol Cell Biol* 3, 475-486.

Laflamme M A, Zbinden S, Epstein S E & Murry C E. (2007). Cell-based therapy for myocardial ischemia and infarction: pathophysiological mechanisms. *Annu Rev Pathol* 2, 307-339.

Lambert J M, Lopez E F & Lindsey M L. (2008). Macrophage roles following myocardial infarction. *Int J Cardiol* 130, 147-158.

Latronico M V, Costinean S, Lavitrano M L, Peschle C & Condorelli G. (2004). Regulation of cell size and contractile function by AKT in cardiomyocytes. *Ann N Y Acad Sci* 1015, 250-260.

Lefer D J & Granger D N. (2000). Oxidative stress and cardiac disease. *Am J Med* 109, 315-323.

MacLellan W R & Schneider M D. (1997). Death by design. Programmed cell death in cardiovascular biology and disease. *Circ Res* 81, 137-144.

Mansson-Broberg A, Siddiqui A J, Genander M, Grinnemo K H, Hao X, Andersson A B, Wardell E, Sylven C & Corbascio M. (2008). Modulation of ephrinB2 leads to increased angiogenesis in ischemic myocardium and endothelial cell proliferation. *Biochem Biophys Res Commun* 373, 355-359.

Matsui T, Nagoshi T & Rosenzweig A. (2003). Akt and PI 3-kinase signaling in cardiomyocyte hypertrophy and survival. *Cell Cycle* 2, 220-223.

Matsui T & Rosenzweig A. (2005). Convergent signal transduction pathways controlling cardiomyocyte survival and function: the role of PI 3-kinase and Akt. *J Mol Cell Cardiol* 38, 63-71.

Mellitzer G, Xu Q & Wilkinson D G. (1999). Eph receptors and ephrins restrict cell intermingling and communication. *Nature* 400, 77-81.

Meloni M, Caporali A, Graiani G, Lagrasta C, Katare R, Van Linthout S, Spillmann F, Campesi I, Madeddu P, Quaini F & Emanueli C. Nerve growth factor promotes cardiac repair following myocardial infarction. *Circ Res* 106, 1275-1284.

Milavetz J J, Giebel D W, Christian T F, Schwartz R S, Holmes D R, Jr. & Gibbons R J. (1998). Time to therapy and salvage in myocardial infarction. *J Am Coll Cardiol* 31, 1246-1251.

Miura T & Mild T. (2008). Limitation of myocardial infarct size in the clinical setting: current status and challenges in translating animal experiments into clinical therapy. *Basic Res Cardiol* 103, 501-513.

Miyamoto S, Murphy A N & Brown J H. (2009). Akt mediated mitochondrial protection in the heart: metabolic and survival pathways to the rescue. *J Bioenerg Biomembr* 41, 169-180.

Moon J J, Lee S H & West J L. (2007). Synthetic Biomimetic Hydrogels Incorporated with Ephrin-A1 for Therapeutic Angiogenesis. *Biomacromolecules* 8, 42-49.

Munoz J J, Alfaro D, Garcia-Ceca J, Alonso C L, Jimenez E & Zapata A. (2006). Thymic alterations in EphA4-deficient mice. *J Immunol* 177, 804-813.

Murray D B, Gardner J D, Brower G L & Janicki J S. (2004). Endothelin-1 mediates cardiac mast cell degranulation, matrix metalloproteinase activation, and myocardial remodeling in rats. *Am J Physiol Heart Circ Physiol* 287, H2295-2299.

Nageh T, Sherwood R A, Harris B M, Byrne J A & Thomas M R. (2003). Cardiac troponin T and I and creatine kinase-MB as markers of myocardial injury and predictors of outcome following percutaneous coronary intervention. *Int J Cardiol* 92, 285-293.

Nah D Y & Rhee M Y. (2009). The inflammatory response and cardiac repair after myocardial infarction. *Korean Circ J* 39, 393-398.

Nakai A, Yamaguchi O, Takeda T, Higuchi Y, Hikoso S, Taniike M, Omiya S, Mizote I, Matsumura Y, Asahi M, Nishida K, Hori M, Mizushima N & Otsu K. (2007). The role of autophagy in cardiomyocytes in the basal state and in response to hemodynamic stress. *Nat Med* 13, 619-624.

Nicholson D W, Ali A, Thornberry N A, Vaillancourt J P, Ding C K, Gallant M, Gareau Y, Griffin P R, Labelle M, Lazebnik Y A & et al. (1995). Identification and inhibition of the ICE/CED-3 protease necessary for mammalian apoptosis. *Nature* 376, 37-43.

Ogawa K, Pasqualini R, Lindberg R A, Kain R, Freeman A L & Pasquale E B. (2000). The ephrin-A1 ligand and its receptor, EphA2, are expressed during tumor neovascularization. *Oncogene* 19, 6043-6052.

Oliver F J, de la Rubia G, Rolli V, Ruiz-Ruiz M C, de Murcia G & Murcia J M. (1998). Importance of poly(ADP-ribose) polymerase and its cleavage in apoptosis. Lesson from an uncleavable mutant. *J Biol Chem* 273, 33533-33539.

Oyama M A & Sisson D D. (2004). Cardiac troponin-I concentration in dogs with cardiac disease. *J Vet Intern Med* 18, 831-839.

Pandey A, Shao H, Marks R M, Polverini P J & Dixit V M. (1995). Role of B61, the ligand for the Eck receptor tyrosine kinase, in T NF-alpha-induced angiogenesis. *Science* 268, 567-569.

Pasquale E B. (2008). Eph-ephrin bidirectional signaling in physiology and disease. *Cell* 133, 38-52.

Pasquale E B. (2010). Eph receptors and ephrins in cancer: bidirectional signalling and beyond. *Nat Rev Cancer* 10, 165-180.

Patten R D & Karas R H. (2006). Estrogen replacement and cardiomyocyte protection. *Trends Cardiovasc Med* 16, 69-75.

Pfeffer M A & Braunwald E. (1991). Ventricular enlargement following infarction is a modifiable process. *Am J Cardiol* 68, 127D-131D.

Porrello E R & Delbridge L M. (2009). Cardiomyocyte autophagy is regulated by angiotensin II type 1 and type 2 receptors. *Autophagy* 5, 1215-1216.

Reed J C, Zha H, Aime-Sempe C, Takayama S & Wang H G. (1996). Structure-function analysis of Bcl-2 family proteins. Regulators of programmed cell death. *Adv Exp Med Biol* 406, 99-112.

Segers V F & Lee R T. Protein Therapeutics for Cardiac Regeneration after Myocardial Infarction. *J Cardiovasc Transl Res*.

Shaut C A, Saneyoshi C, Morgan E A, Knosp W M, Sexton D R & Stadler H S. (2007). HOXA13 directly regulates EphA6 and EphA7 expression in the genital tubercle vascular endothelia. *Dev Dyn* 236, 951-960.

Shujia J, Haider H K, Idris N M, Lu G & Ashraf M. (2008). Stable therapeutic effects of mesenchymal stem cell-based multiple gene delivery for cardiac repair. *Cardiovasc Res* 77, 525-533.

Siddiqui A J, Fischer H, Widegren U, Grinnemo K H, Hao X, Mansson-Broberg A, Sylven C & Gustafsson T. Depressed expression of angiogenic growth factors in the subacute phase of myocardial ischemia: a mechanism behind the remodeling plateau? *Coron Artery Dis* 21, 65-71.

Siragusa M, Katare R, Meloni M, Damilano F, Hirsch E, Emanueli C & Madeddu P. Involvement of phosphoinositide 3-kinase gamma in angiogenesis and healing of experimental myocardial infarction in mice. *Circ Res* 106, 757-768.

Slezak J, Tribulova N, Okruhlicova L, Dhingra R, Bajaj A, Freed D & Singal P. (2009). Hibernating myocardium: pathophysiology, diagnosis, and treatment. *Can J Physiol Pharmacol* 87, 252-265.

Stadler H S, Higgins K M & Capecchi M R. (2001). Loss of Eph-receptor expression correlates with loss of cell adhesion and chondrogenic capacity in Hoxa13 mutant limbs. *Development* 128, 4177-4188.

Tang S C. (2002). BAG-1, an anti-apoptotic tumour marker. IUBMB Life 53, 99-105. Terman A & Brunk U T. (2005). Autophagy in cardiac myocyte homeostasis, aging, and pathology. *Cardiovasc Res* 68, 355-365.

Tewari M, Quan L T, O'Rourke K, Desnoyers S, Zeng Z, Beidler D R, Poirier G G, Salvesen G S & Dixit V M. (1995). Yama/CPP32 beta, a mammalian homolog of CED-3, is a CrmA-inhibitable protease that cleaves the death substrate poly(ADP-ribose) polymerase. *Cell* 81, 801-809.

Townsend P A, Cutress R I, Carroll C J, Lawrence K M, Scarabelli T M, Packham G, Stephanou A & Latchman D S. (2004). BAG-1 proteins protect cardiac myocytes from simulated ischemia/reperfusion-induced apoptosis via an alternate mechanism of cell survival independent of the proteasome. *J Biol Chem* 279, 20723-20728.

Urbich C, Rossig L & Dimmeler S. (2006). Restoration of cardiac function with progenitor cells. *Novartis Found Symp* 274, 214-223; discussion 223-217, 272-216.

van Rooij E, Marshall W S & Olson E N. (2008). Toward microRNA-based therapeutics for heart disease: the sense in antisense. *Circ Res* 103, 919-928.

Virag J I, Dries J L, Easton P R, Friesland A M, DeAntonio J H, Chintalgattu V, Cozzi E, Lehman B D, Ding J M & Lust R M. (2010). Attenuation of Myocardial Injury in Mice with Functional Deletion of the Circadian Rhythm Gene mPer2. *Am J Physiol Heart Circ Physiol Epub Ahead of Print*.

Virag J I & Murry C E. (2003). Myofibroblast and endothelial cell proliferation during murine myocardial infarct repair. *Am J Pathol* 163, 2433-2440.

Wang L F, Fokas E, Juricko J, You A, Rose F, Pagenstecher A, Engenhart-Cabillic R & An H X. (2008). Increased expression of EphA7 correlates with adverse outcome in primary and recurrent glioblastoma multiforme patients. *BMC Cancer* 8, 79.

Whelan R S, Kaplinskiy V & Kitsis R N. Cell death in the pathogenesis of heart disease: mechanisms and significance. *Annu Rev Physiol* 72, 19-44.

Wykosky J & Debinski W. (2008). The EphA2 receptor and ephrinA1 ligand in solid tumors: function and therapeutic targeting. *Mol Cancer Res* 6, 1795-1806, Wykosky J, Gibo D M, Stanton C & Debinski W. (2005). EphA2 as a novel molecular marker and target in glioblastoma multiforme. *Mol Cancer Res* 3, 541-551.

Wykosky J, Palma E, Gibo D M, Ringler S, Turner C P & Debinski W. (2008). Soluble monomeric EphrinA1 is released from tumor cells and is a functional ligand for the EphA2 receptor. *Oncogene* 27, 7260-7273.

Zhou R. (1998). The Eph family receptors and ligands. *Pharmacol Ther* 77, 151-181.

---

What is claimed is:

1. A method of reducing injury caused by myocardial infarction in a subject in need thereof, comprising administering to the subject a therapeutically effective amount of an ephrin, wherein the ephrin is ephrin A1, ephrinA1-Fc or a combination thereof.

2. The method of claim 1, wherein the ephrin is ephrin A1.

3. The method of claim 1, wherein the ephrin comprises ephrinA1-Fc.

4. The method of claim 1, wherein the injury is infarct size, necrosis, chamber dilation, wall thinning, inflammation, apoptotic cell death, autophagy, hypertrophy, fibrosis, or a combination thereof.

5. The method of claim 1, wherein the ephrin is administered at the time of myocardial infarction.

6. A method of promoting myocardial repair following myocardial injury in a subject in need thereof, comprising administering to the subject a therapeutically effective amount of an ephrin, wherein the ephrin is ephrin A1, ephrinA1-Fc or a combination thereof.

7. The method of claim 6, wherein the ephrin is ephrin A1.

8. The method of claim 6, wherein the ephrin comprises ephrinA1 Fc.

9. The method of claim 6, wherein the myocardial repair is either an improvement or a decrease in infarct size, necrosis, apoptosis, autophagy, angiogenesis, chamber dilation, wall thinning, inflammation, reduction in serum cardiac troponin and/or other markers of cardiomyocyte degradation, or a combination thereof.

10. The method of claim 6, wherein the ephrin is administered at the time of myocardial injury.

11. The method of claim 6, wherein the ephrin is administered as an adjunct to reperfusion therapy.

12. The method of claim 11, wherein the ephrin is administered before reperfusion therapy.

* * * * *

UNITED STATES PATENT AND TRADEMARK OFFICE
CERTIFICATE OF CORRECTION

| | | |
|---|---|---|
| PATENT NO. | : 8,580,739 B2 | Page 1 of 1 |
| APPLICATION NO. | : 13/299096 | |
| DATED | : November 12, 2013 | |
| INVENTOR(S) | : Virag et al. | |

It is certified that error appears in the above-identified patent and that said Letters Patent is hereby corrected as shown below:

In the Specification:

Column 3, Line 41: Correct "j different from control,"
to read -- † different from control, --

Column 5, Lines 28-30: Correct "or "ephrins" (erythropoietin-producing hepatocellular (Eph)/Eph receptor interacting proteins refers to"
to read -- or "ephrins" (erythropoietin-producing hepatocellular (Eph)/Eph receptor interacting proteins) refers to --

Column 6, Line 23: Correct "Nos. X_001141980.2 and"
to read -- Nos. XP_001141980.2 and --

Column 6, SEQ ID NO: 3, at location 151-160: Correct "ithspqandn"
to read -- ithspqahdn --

Column 23, Line 63: Correct "Fume C,"
to read -- Furne C, --

Signed and Sealed this
Thirtieth Day of September, 2014

Michelle K. Lee
*Deputy Director of the United States Patent and Trademark Office*